(12) United States Patent
Hansen

(10) Patent No.: US 11,780,207 B2
(45) Date of Patent: Oct. 10, 2023

(54) ELASTIC NONWOVEN FABRIC SHEETS AND METHODS FOR MAKING THE SAME

(71) Applicant: FIBERTEX PERSONAL CARE A/S, Aalborg Ost (DK)

(72) Inventor: Morten Rise Hansen, Aalborg (DK)

(73) Assignee: FIBERTEX PERSONAL CARE A/S, Aalborg Ost (DK)

( * ) Notice: Subject to any disclaimer, the term of this patent is extended or adjusted under 35 U.S.C. 154(b) by 109 days.

(21) Appl. No.: 17/295,068

(22) PCT Filed: Feb. 26, 2020

(86) PCT No.: PCT/EP2020/055002
§ 371 (c)(1),
(2) Date: May 19, 2021

(87) PCT Pub. No.: WO2020/187540
PCT Pub. Date: Sep. 24, 2020

(65) Prior Publication Data
US 2021/0355614 A1  Nov. 18, 2021

(30) Foreign Application Priority Data
Mar. 15, 2019  (EP) .................... 19163084

(51) Int. Cl.
*B32B 5/26* (2006.01)
*A61F 13/15* (2006.01)
(Continued)

(52) U.S. Cl.
CPC ........ *B32B 5/267* (2021.05); *A61F 13/15577* (2013.01); *A61F 13/47263* (2013.01);
(Continued)

(58) Field of Classification Search
CPC .......... B32B 5/022; B32B 5/26; B32B 5/266; D04H 3/16; D04H 1/43918; D04H 3/00; D04H 3/018; A61F 13/15
See application file for complete search history.

(56) References Cited

U.S. PATENT DOCUMENTS 6,001,460 A * 12/1999 Morman ................. B32B 37/08
                                                    428/200
6,454,989 B1   9/2002 Neely et al.
(Continued)

FOREIGN PATENT DOCUMENTS

EP    2116367 A1    11/2009
EP    3290014 A1 *  3/2018 ............... D04H 3/07
(Continued)

OTHER PUBLICATIONS https://acmemills.com/ thermal-bonding-process-of-nonwoven-methods-of-thermal-bonding-marketing-position-of-thermal-bonded-nonwoven/ downloaded Feb. 5, 2023 (Year: 2023).*
(Continued)

*Primary Examiner* — Jennifer A Steele
(74) *Attorney, Agent, or Firm* — Kilyk & Bowersox, P.L.L.C.

(57) ABSTRACT

The invention relates to a nonwoven fabric sheet comprising at least two adjacent layers of spunbonded nonwoven webs, one of which is an elastic layer in the form of a spunbonded nonwoven web comprising elastic fibers formed from a thermoplastic elastomer polymer material. The invention further relates to a method of manufacturing such nonwoven and the use of such nonwoven.

21 Claims, 16 Drawing Sheets

Figure 1:
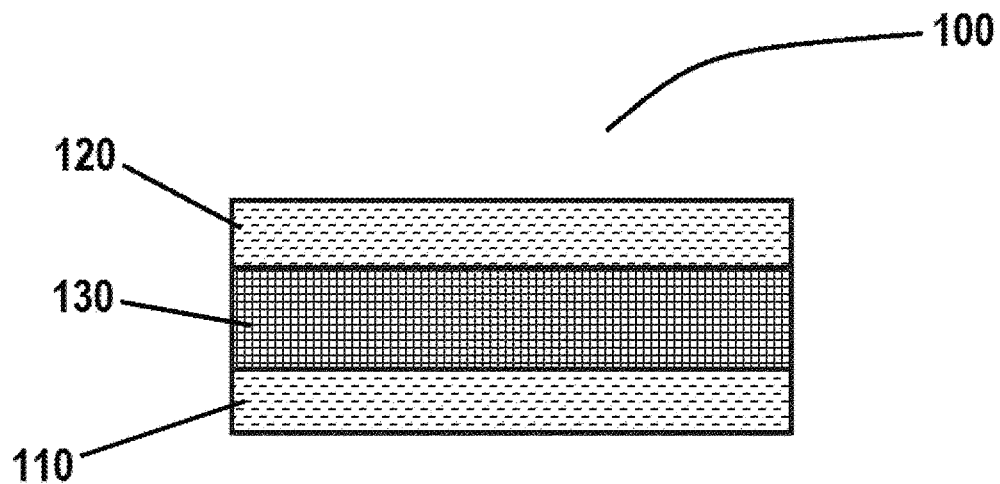

(51) Int. Cl.
*A61F 13/49* (2006.01)
*D04H 3/14* (2012.01)
*D04H 3/007* (2012.01)
*A61F 13/472* (2006.01)
*A61F 13/51* (2006.01)
*D04H 3/005* (2012.01)
*D04H 1/4391* (2012.01)
*D04H 1/4291* (2012.01)
*D04H 1/4374* (2012.01)
*D04H 1/44* (2006.01)
*D04H 1/70* (2012.01)
*D04H 3/16* (2006.01)
*A61F 13/496* (2006.01)

(52) U.S. Cl.
CPC ....... *A61F 13/4902* (2013.01); *D04H 1/4291* (2013.01); *D04H 1/4374* (2013.01); *D04H 1/43918* (2020.05); *D04H 1/44* (2013.01); *D04H 1/70* (2013.01); *D04H 3/005* (2013.01); *D04H 3/007* (2013.01); *D04H 3/14* (2013.01); *D04H 3/16* (2013.01); *A61F 13/496* (2013.01); *A61F 2013/15959* (2013.01); *A61F 2013/15991* (2013.01); *A61F 2013/51026* (2013.01)

(56) References Cited

U.S. PATENT DOCUMENTS

| | | | | |
|---|---|---|---|---|
| 10,894,384 | B2 * | 1/2021 | Sommer | B32B 5/10 |
| 2003/0124331 | A1 * | 7/2003 | Morell | B32B 27/02 |
| | | | | 428/297.4 |
| 2004/0097154 | A1 * | 5/2004 | Bansal | D04H 3/14 |
| | | | | 442/345 |
| 2004/0127128 | A1 * | 7/2004 | Thomas | D04H 1/593 |
| | | | | 442/361 |
| 2006/0135021 | A1 * | 6/2006 | Calhoun | D01F 8/06 |
| | | | | 442/364 |
| 2007/0135008 | A1 * | 6/2007 | Hall | B32B 27/12 |
| | | | | 442/181 |
| 2010/0105273 | A1 * | 4/2010 | Motomura | D04H 3/005 |
| | | | | 442/329 |
| 2016/0221300 | A1 | 8/2016 | Sommer et al. | |
| 2017/0335498 | A1 * | 11/2017 | Hansen | D04H 1/56 |
| 2018/0002850 | A1 | 1/2018 | Hansen et al. | |
| 2018/0038025 | A1 * | 2/2018 | Takaku | A41D 13/11 |
| 2018/0271717 | A1 * | 9/2018 | Dria | D04H 3/018 |
| 2019/0136426 | A1 | 5/2019 | Hansen et al. | |

FOREIGN PATENT DOCUMENTS

| | | | | |
|---|---|---|---|---|
| EP | 3290014 | A1 | 3/2018 | |
| GB | 2126162 | A * | 3/1984 | ............. A47L 13/16 |
| WO | 9621562 | A1 | 7/1996 | |
| WO | WO-9621562 | A1 * | 7/1996 | ............. D04H 1/52 |
| WO | WO-0037723 | A2 * | 6/2000 | ............. B32B 5/022 |
| WO | 02052085 | A2 | 7/2002 | |
| WO | 2009032865 | A1 | 3/2009 | |
| WO | 2010039583 | A1 | 4/2010 | |
| WO | 2018183315 | A1 | 10/2018 | |

OTHER PUBLICATIONS

INDA Association of Nonwovens Fabrics Industry Glossary; copyright 2002 INDA, Association of the Nonwovens Fabric Industry (Year: 2002).*

International Search Report and Written Opinion issued in corresponding International Patent Application No. PCT/EP2020/055002 dated Mar. 30, 2020 (13 pages).

* cited by examiner

ELASTIC NONWOVEN FABRIC SHEETS AND METHODS FOR MAKING THE SAME

This application is a National Stage Application of PCT/EP2020/055002, filed Feb. 26, 2020, which claims priority to European Patent Application No. 19163084.7, filed Mar. 15, 2019.

The invention relates to nonwoven fabric sheets having elastic properties, to methods of manufacturing such nonwoven fabrics and to uses for such nonwoven fabrics.

In the hygiene industry nonwoven materials are frequently used, for example in the manufacture of diapers and adult incontinence products, where the nonwoven materials may serve, for example, as backsheets. Spunbonded sheets or multilayer sheets comprising spunbonded layers have been proven very useful and economically feasible.

For some applications, for example when making back-ears in open diapers or waist belt portions in pant-like diapers, it would be very desirable that the nonwoven materials have elastic properties. However, previously known spunbonded nonwoven materials may have some extensibility, but are hardly elastic in the sense that they more or less fully retract to their original state after being stretched.

For this reason, in the context of back-ears in open diapers, solid sheets of elastic materials have frequently been laminated between outer nonwoven layers and the arrangement glued together. An exemplary material is disclosed in WO 2018/183315 A1. The gluing, however, involves a separate process in manufacture and the laminates are largely air-impermeable and may have a stiff touch.

In the context of waist belt portions, elastic strands have frequently been laminated between two layers of nonwoven materials in the respective portions of the products. Apart from the more complex makeshift, such elastic strands often make products uncomfortable to wear and can lead to red marks on the skin.

In EP 2 342 075 A1 a process of making a nonwoven fabric having inherent elastic properties is disclosed, where an elastic layer of meltblown elastic fibers is sandwiched between layers of spunlaced webs, that are formed from staple fibers by carding and hydro-entanglement. The spunlaced webs typically have good extensibility in cross-machine direction but are relatively expensive to produce and have limitations in terms of lowest obtainable basis weights and process speeds. The meltblown elastic engine has good elastic properties but may be very dense and subject to limitations in terms of highest obtainable fiber diameters, basis weights and hence stability.

The invention aims to provide an inherently elastic nonwoven fabric sheet that is easy to produce and has excellent properties.

Against this background, the invention suggests a nonwoven fabric sheet comprising at least two adjacent layers of spunbonded nonwoven webs, wherein a first one of the two layers is a carrier layer in the form of a spunbonded nonwoven web comprising crimped multicomponent fibers, and wherein a second one of the two layers is an elastic layer in the form of a spunbonded nonwoven web comprising elastic fibers formed from a thermoplastic elastomer polymer material.

The web of the carrier layer comprises a pattern of macroscopic bonding points, while the web of the elastic layer is devoid of macroscopic bonding points. The web of the carrier layer may be provided as prefabricated web. Hence, thermal bonding of these webs by known bonding processes like calendering can be done individually and without the need to also bond the elastic layer at the same time. This is advantageous because bonding the entire fabric would render the fabric tighter and could hence be detrimental to elasticity.

The processes of bonding the layers together can be omitted because of an inherent stickiness of the elastic fibers during the first couple of seconds after they are spun. This stickiness leads to a good adherence of the layers and overall stability of the fabric despite the lack of bonding the layers together.

Preferably, in this context, the fabric sheet is also devoid of any needling pattern that results from needling together the carrier and elastic layers, and also of any resulting pattern or structure of other bonding techniques, like ultrasonic bonding, hydro-entanglement and similar.

Preferably, the nonwoven fabric sheet of this invention comprises at least three adjacent layers of spunbonded nonwoven webs, wherein a third one of the three layers is also a carrier layer in the form of a spunbonded nonwoven web comprising crimped multicomponent fibers, and wherein the elastic layer is sandwiched between the two carrier layers. In this context, it is understood that the nonwoven fabric sheet can also comprise more than three layers. One example is a nonwoven fabric sheet comprising two elastic layers and two layers of spunbonded nonwoven webs.

In the carrier layer(s), a first component of the crimped multicomponent fibers, preferably bicomponent fibers consists of a first thermoplastic polymer material and a second component of the multicomponent fibers consists of a second thermoplastic polymer material that is different from the first thermoplastic polymer material. Useful polymer materials are generally polyolefins like polypropylene (PP), polyethylene (PE) or polypropylene-ethylene copolymers (co-PP). For example, the first component may be PP and the second component may be a different PP (PP/PP). In another example, the first component may be PP and the second component may be co-PP (PP/co-PP). In yet another example, the first component may be PP and the second component may be PE (PP/PE). In either case, part or even all of a polyolefin of a component may be replaced by a renewable polymer like starch (e.g. from maize or sugarcane).

The two components may be arranged side-by-side or in an eccentric sheath-core manner over the cross-section of the fibers. The different behavior of the different thermoplastic polymer materials leads to crimp after the quenching and stretching of the fibers in the spunbonding process. Producing nonwoven webs from crimped fibers per se is well-known in the art and disclosed, for example, U.S. Pat. No. 6,454,989 B1. Newer technologies that lead to very soft products are disclosed, for example, in EP 3 054 042 A1, EP 3 246 443 A1, EP 3 246 444 A1 and WO 2017/198336 A1.

The first and/or the second carrier layer may be formed exclusively from the crimped multicomponent fibers in the sense that it comprises no other fibers, for example no standard uncrimped monocomponent fibers, or may be formed from a mixture of crimped multicomponent fibers and uncrimped monocomponent fibers. In the case of a mixture, the content of the crimped multicomponent fibers is preferably higher than 50 wt. %, more preferably higher than 70 wt. % and still more preferably higher than 90 wt. %.

In one embodiment, the average crimp number of the crimped multicomponent fibers is in the range of at least 5 and preferably at least 8 crimps per cm in the fiber, as measured per Japanese standard JIS L-1015-1981 under a pre-tension load of 2 mg/denier.

The carrier layers are responsible for a textile feel and, due to the use of crimped fibers, have a certain extensibility that goes beyond the extensibility of standard spunbonded webs on the basis of uncrimped monocomponent fibers. Specifically, while standard spunbonded webs on the basis of uncrimped monocomponent fibers typically have an elongation at break of around 45-50% in machine direction and around 55-65% in cross-machine direction when measured according to WSP 100.4, lofty spunbonded nonwoven webs on the basis of crimped multicomponent fibers may have elongation values of beyond 100% in machine direction and even higher values in cross-machine direction, typically above 200%.

The elastic layer of spunbonded thermoplastic elastomer (TPE) fibers has a relatively high stability due to the possibility of relatively easy variation of the basis weight over a wide range. At the same time, the fibers are comparatively thick and result in stable and relatively open fabrics. The elastic layer may consist exclusively of fibers formed from a thermoplastic elastomer material or may at least comprise a significant portion, e.g. more than 60 wt.-% or more than 80 wt.-% of fibers formed from a thermoplastic elastomer material.

In one embodiment, the nonwoven fabric sheets of the invention consist of the two carrier layers and the elastic layer in between.

The basis weight of the or each carrier layer may be between 5-40 $g/m^2$, preferably between 8-30 $g/m^2$, more preferably between 8-25 $g/m^2$ and yet more preferably between 10-20 $g/m^2$. The basis weight of the elastic layer may be between 10-140 $g/m^2$, preferably between 20-120 $g/m^2$ and more preferably between 25 and 100 $g/m^2$. These basis weights have proven useful in terms of fabric touch, elastic properties and stability.

The overall thickness of the nonwoven fabric sheet is preferably less than 1.20 mm as determined according to WSP120.6. Such materials of the invention typically have sufficient mechanical stability to be added in diaper products. At the same time, a thin material is beneficial to an overall less bulky and regular brief-like appearance of such products.

In one embodiment, the webs of both carrier layers comprise a pattern of macroscopic bonding points. The webs of both carrier layers may be provided as prefabricated webs.

In a preferred variant, the bonding pattern of the carrier layer(s) is relatively open, meaning that the number of bonding points per $cm^2$ of fabric surface may be lower than 30 and/or that the total area of the fabric surface taken up by the areal bonding points is less than 18% and preferably less than 15%.

One preferred way of loosening the tight structure for the carrier layers and exposing the elasticity of the elastic layers comprises treating the overall nonwoven fabric sheet, which comprises the at least two adjacent layers of spunbonded nonwoven webs, in a so-called ring-rolling process described in more detail in connection with the inventive method further below. As a consequence, the fabric sheet may be configured such that at least portions of the fabric are activated and comprise alternating macroscopic zones of different microscopic fiber configuration, wherein the zones are in the form of parallel and preferably uninterrupted stripes oriented in lengthwise direction of the fabric sheet. By ring-rolling, the elongation at break in cross-machine direction of the fabric sheet may be increased to values of beyond 200% or even beyond 300% when measured according to WSP 100.4. At the same time, the elasticity and extensibility in machine direction of the fabric sheet is hardly influenced and a relatively lower extensibility in machine direction may be very helpful during converting of the fabric sheet during its application in, for example, hygiene article manufacture.

Another preferred way of loosening the tight structure for the carrier layers and exposing the elasticity of the elastic layers comprises treating the overall nonwoven fabric sheet, which comprises the at least two adjacent layers of spunbonded nonwoven webs, in a process for lengthwise activation using cross-bladed mill activation also described in more detail in connection with the inventive method further below. As a consequence, the fabric sheet may preferably be configured such that at least portions of the fabric are activated and comprise alternating macroscopic zones of different microscopic fiber configuration, the zones in this case being in the form of parallel stripes oriented in cross direction of the fabric sheet. By was of such lengthwise activation, the elongation at break in machine direction of the fabric sheet may be increased to values of beyond 150% or even beyond 200% when measured according to WSP 100.4. At the same time, the elasticity and extensibility in cross direction of the fabric sheet is hardly influenced.

In one embodiment, the accordingly treated fabric sheet may comprise portions such as machine-directional bands of activated material of higher elasticity and other portions such as intermediate machine-directional bands of unactivated material having lower elasticity. In other words, the fabric may comprise at least one machine-directional band of activated material and at least one adjacent machine-directional band of undactivated material, ore more alternating machine-directional bands or activated and unactivated material. Such can result from only partial activation of the fabric sheet, as described in more detail in connection with the inventive method further below.

In one embodiment, the thermoplastic elastomer polymer material forming for the elastic fibers of the elastic layer is a thermoplastic polyolefin elastomer material (TPE-o), preferably a thermoplastic polyolefin elastomer material comprising propylene-α-olefin copolymers. The content of the propylene-α-olefin copolymers within the thermoplastic material may in one embodiment be at least 80 wt.-%. Suitable TPE-o materials for use in the context of the present invention are disclosed in EP 2 342 075 A1. Alternatively or additionally, meaning as a mixture, to a thermoplastic polyolefin elastomer material, other thermoplastic elastomer materials like especially thermoplastic polyurethanes (TPU), styrenic block copolymers (TPE-s) may be used.

In one embodiment, a bicomponent elastic fiber can be formed from two different thermoplastic elastomers, arranged, for example, in a side-by-side or sheath-core configuration. In such arrangement, elastic properties of two different thermoplastic elastomers can be combined within the fibers. Also, depending on the configuration, a certain crimp level can be attributed to also the elastic fibers, if desired. For example, both components can be made up from TPE-o, preferably a thermoplastic polyolefin elastomer material comprising propylene-α-olefin copolymers. The content of the propylene-α-olefin copolymers within the thermoplastic material may be different between the two components.

In one embodiment, up to 20 wt.-% and preferably up to 10 wt.-% of a thermoplastic olefin, such as a homo polypropylene may be added to the thermoplastic elastomer. In some cases this can be beneficial to alter the crystallization behaviour and hence stickiness and elastic performance.

As already mentioned further above, the elastic fibers resulting from spinning such thermoplastic elastomer materials are, at least immediately after the spinning, typically relatively sticky as an inherent property. Consequently, the elastic layer as a whole is inherently sticky and adheres well to the carrier layer(s) without the need for any additional glue, especially if a mild pre-compaction step or the like is used during manufacture to additionally promote adhesion. Hence, in a preferred embodiment, the nonwoven fabric does not comprise any glue between the adjacent carrier and elastic layers. This is advantageous because the addition of glue comes with additional material cost and process steps. Still further, volatile glue components can be smelled on the products and glue is undesirable under environmental aspects.

The invention further relates to a method for manufacturing a nonwoven fabric sheet according to the invention, wherein the method comprises: (a) providing a first spunbonded nonwoven web comprising crimped multicomponent fibers, which corresponds to a carrier layer of the fabric sheet to be formed; and (b) spinning and laying elastic fibers onto the first web to form the elastic layer of the fabric sheet.

The spinning of step (b) involves extruding, quenching and drawing the elastic fibers in a spunbonding machine. The first web is typically conveyed to the spunbonding machine on a conveyor belt.

The first web is preferably provided by unrolling from a roll of prefabricated material. The web is typically unrolled to the conveyor belt and advances to the spunbonding machine. The prefabricated material may be a multilayer material comprising one or more spunbonded webs comprising crimped fibers or simply a one layer spunbonded web comprising crimped fibers. It is typically bonded by, for example, calendering and comprises a macroscopic bonding pattern. Suitable multilayer materials comprising, for example, two, three or four individual layers of spunbonded material can comprise layers of different crimp level.

In one embodiment, the method further comprises a step (c) of superimposing a second spunbonded nonwoven web comprising crimped multicomponent fibers to the exposed side of the elastic layer to form for another carrier layer of the fabric sheet. In this variant of the method, sheets according to preferred embodiments of the invention are provided, which have a sandwich structure of an elastic layer interposed between two carrier layers.

Also the second web may be provided by unrolling from a roll of prefabricated material. Hence, a prefabricated second web is directly laid onto the exposed side of the elastic layer as the sheet comprising the first carrier layer and the elastic layer advance on the conveyor belt, typically immediately after the formation of the elastic layer. In this embodiment, both webs that form for the carrier layers may be provided as prefabricated materials.

The prefabricated materials forming for the carrier layers may independently be multilayer materials comprising one ore more spunbonded webs comprising crimped fibers or one layer spunbonded webs comprising crimped fibers. They are typically bonded by, for example, calendering or, if the melting point difference of the components of the multicomponent fibers allows (such as in the case of a PP/PE combination), air through bonding. In the case of calendaring they comprise a macroscopic bonding pattern. For the description of preferred variants we refer to the above description of the inventive fabric sheets.

In an alternative embodiment, the second web may be provided by spinning and laying the fibers forming for the second web directly to the exposed side of the elastic layer. In this embodiment, the second web is not provided as a prefabricated web but rather formed inline by spinning, quenching and drawing crimped bicomponent fibers and optionally further fibers in another spunbonding machine that is arranged downstream the spunbonding machine to form the elastic fibers. The inline formation of the second web typically follows immediately to the formation of the elastic layer.

In one embodiment, the method further comprises a step (d) of pre-compacting the sheet. The step (d) of pre-compacting the sheet occurs after step (b) or, additionally or alternatively, after step (c), if present. It preferably immediately follows the respective step(s) without any step between. Typically, during precompaction (d), the material together with the spinbelt is passed between two preferably unpatterned precompaction rollers. The linear pressure applied is preferably between 3-5 N/mm. The roller temperature may be between 50-110° C. and more preferably between 60-100° C. If temperatures approach the higher end of these ranges, the lamination strength between the layers grows and the fabric tends to assume a relatively flat and less textile touch. This can, however, to some extent be compensated as the material is post activated, e.g. by ring-rolling. In any case, temperature and pressure levels of the precompaction rollers of 60-90° C. and 2-3 N have proven most advantageous in a number of cases and resulted in fabrics with optimized balance between soft touch and lamination strength.

As already mentioned, when describing the inventive sheets, the elastic fibers are sticky and the elastic layer, as a consequence, inherently sticks to the carrier layer(s).

A pre-compaction is hence typically sufficient to hold together the layers of the fabric and the application of glue between the layers typically unnecessary. Hence, in a preferred embodiment, the method of the invention is devoid of any steps for applying glue to the first web before step (b) or to the elastic layer after step (b).

At the same time, also bonding steps like calendering or the like are rendered unnecessary due to the inherent adhesion between the carrier and elastic layers. To the contrary, additional bonding would make the fabrics tighter and run counter the goal of providing sheets of excellent elastic properties. Hence, in another preferred embodiment, the provision of prefabricated webs of crimped fibers aside, the method of the invention is devoid of any bonding steps like calendering.

In one embodiment, the method further comprises a step (e) of mechanically activating the sheet in a mill comprising a pair of interacting rolls whose surfaces comprise interlocking annular grooves and crests. This so-called ring-rolling (e) introduces alternating macroscopic zones of different microscopic fiber configuration that are in the form of parallel and preferably uninterrupted stripes oriented in machine direction of the sheet, as described in more detail above in connection with the inventive sheets. The fabric sheet is thereby activated for increased elasticity, especially in cross-machine direction. Specifically, the structure of the carrier layers is partly broken up and loosened for greater extensibility, while the elastic layer remains largely unaffected. Activating nonwoven sheets by ring-rolling is known and has previously been disclosed, for example, in EP 3 290 014 A1.

In an alternative embodiment, the method further comprises a step (e') of mechanically activating the sheet in a mill comprising a pair of interacting rolls whose surfaces comprise interlocking cross-directional (or, in relation to the rolls, axial) blades. This length-wise activation (e') introduces alternating macroscopic zones of different microscopic fiber configuration that are in the form of parallel stripes oriented in cross-machine direction of the sheet, as described in more detail above in connection with the inventive sheets. The fabric sheet is thereby activated for increased elasticity, especially in machine direction. As with the length-directional ring-rolling activation, also by way of cross-activation the structure of the carrier layers is partly broken up and loosened for greater extensibility, while the elastic layer remains largely unaffected.

As the average fiber orientation in spunbonded webs will inherently be in machine direction, regular uncrimped and inelastic spunbonded webs have a relatively low extensibility in machine direction. When configured and cross-activated in agreement with this invention, however, extensibility before break can be pushed to 150% or even 200% of its original length. Since extensibility requirements in hygiene industry are usually in the range of between 50-100%, this is very much sufficient.

The ring-rolling step (e) or lengthwise activation step (e') may be carried out after step (d), if present, and in one variant immediately follows step (d) without any step between. In another embodiment, step (e) or (e') can also be carried out as a standalone process at a site that is remote from the site where steps (a)-(b) and possibly (c) and/or (d) are carried out. It is hence possible to ship an unactivated material, which may have a comparatively higher density, and to thereby save on space needed for shipping and hence shipping cost.

In one embodiment, the activation may be carried out only to portions of the fabric sheets. For example, ring-rolling may not be carried out over the entire width of the fabric sheet, but only over a certain fraction or certain fractions of the width of the fabric sheet. The same applies to activation using cross-blades, where the blades can extend only over certain fractions of the width of the fabric sheet. This will lead to partially activated fabric sheets that have activated portions of higher elasticity and unactivated portions of lower elasticity. The activated and unactivated portions are in the form of alternating machine-directional bands. Such fabric sheets can potentially by very useful in the manufacture of hygiene products like diapers, where, for example in the ears, elasticity is only desired locally.

The invention yet further relates to the use of a nonwoven fabric sheet according to the invention for the manufacture of a hygiene article. The nonwoven fabric sheets of the invention can be used, for example, in the manufacture of baby diapers or adult incontinence products. They are especially useful for making back-ears in open diapers or waist belt portions in pant-like diapers, where a significant degree of elasticity is required.

In this context, the invention further relates to an open/taped diaper comprising a nonwoven fabric sheet according to the invention as an elastic back ear material. In such application, it is preferred that the fabric sheet material has been activated only on a part of the overall area, with activated portions covering from 30-90% of the full width of the back ear.

Yet further, the invention further relates to a diaper pant for babies or adults, comprising a nonwoven fabric sheet according to the invention as an elastic waist belt material. In such application, it is preferred that the upper waist of such diaper, which is comprised by the inventive material, is folded to form a double layer with a fold width of, for example 0.5-4.5 cm or more preferable 1-4 cm. The fold may be thermally bonded with interrupted spots, ultrasonic bonded or glued. Elastic strands may additionally be introduced in the fold for enhanced performance, if required.

Figure 2:
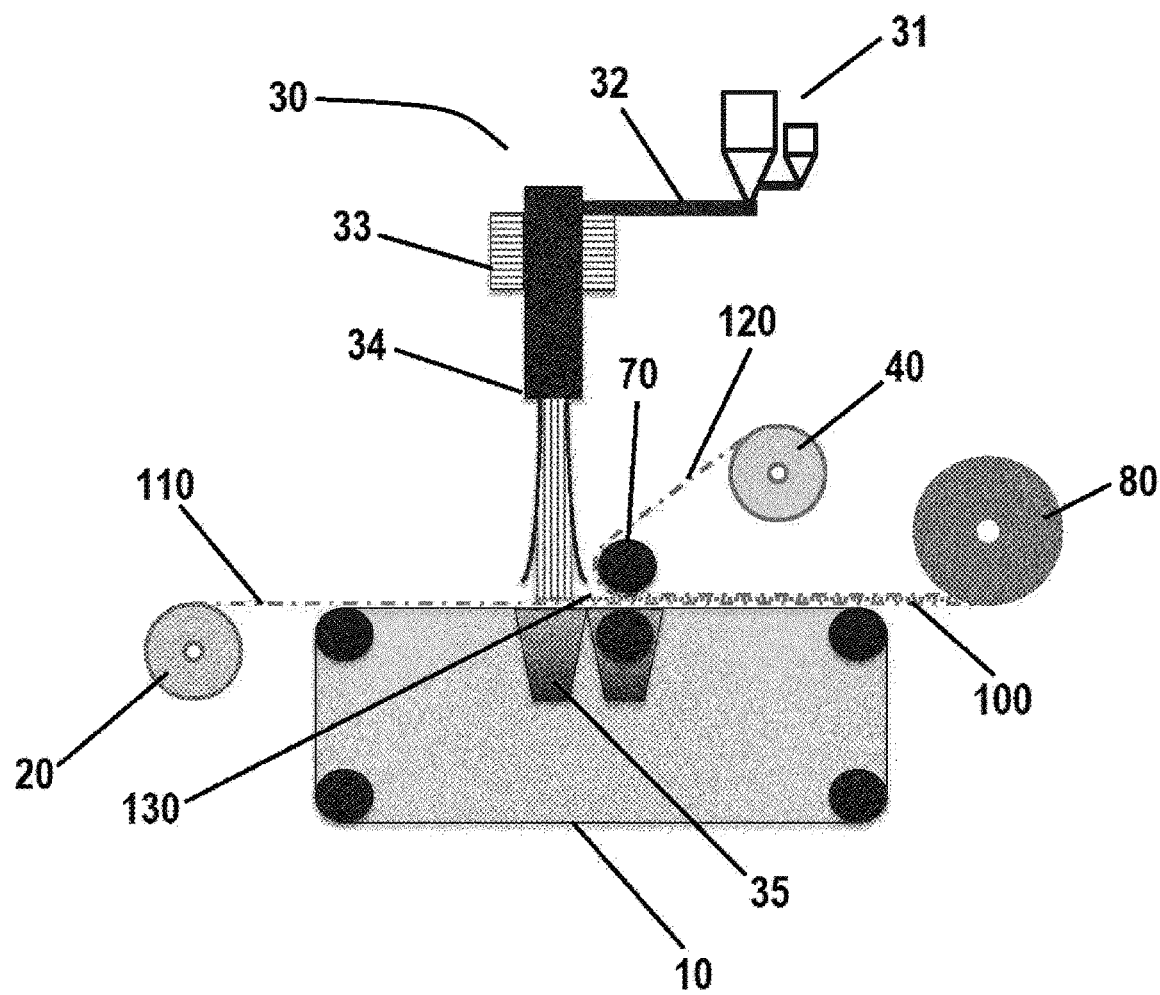
Figure 3:
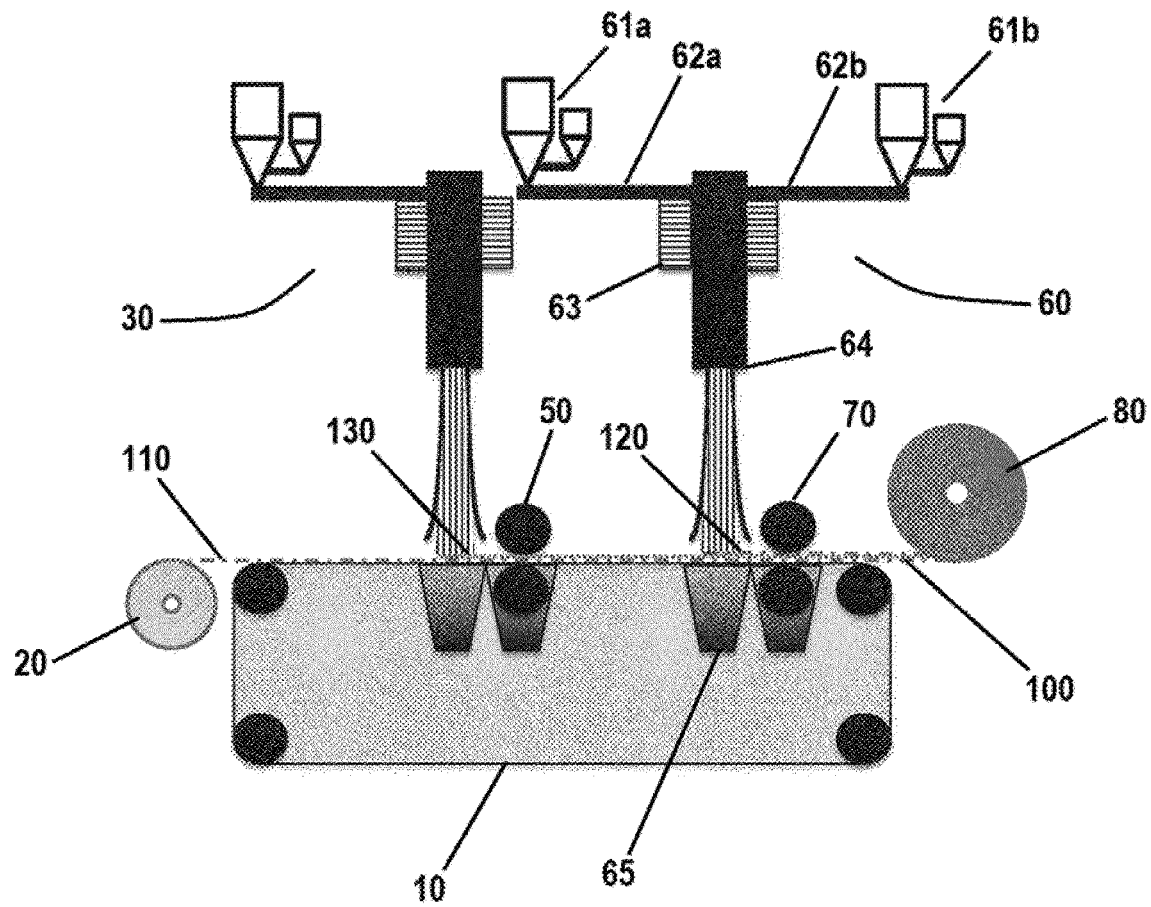
Figure 4:
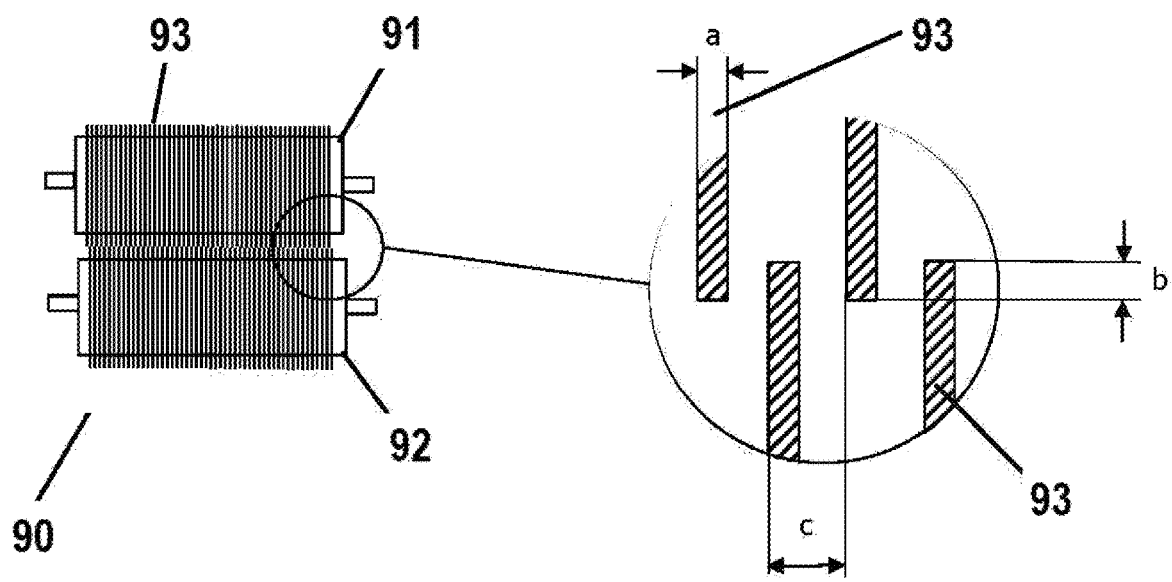
Figure 5:
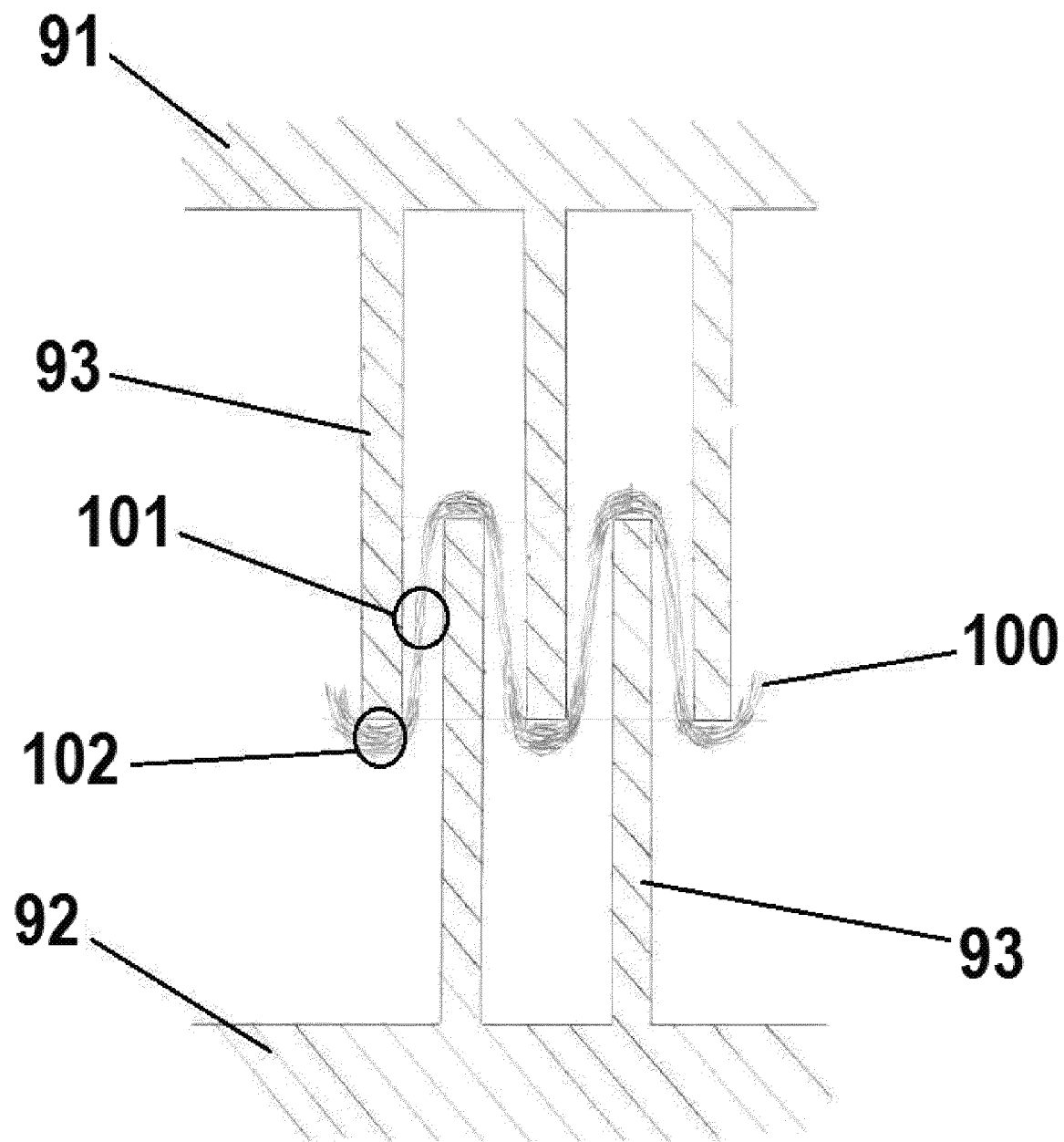
Figure 6:
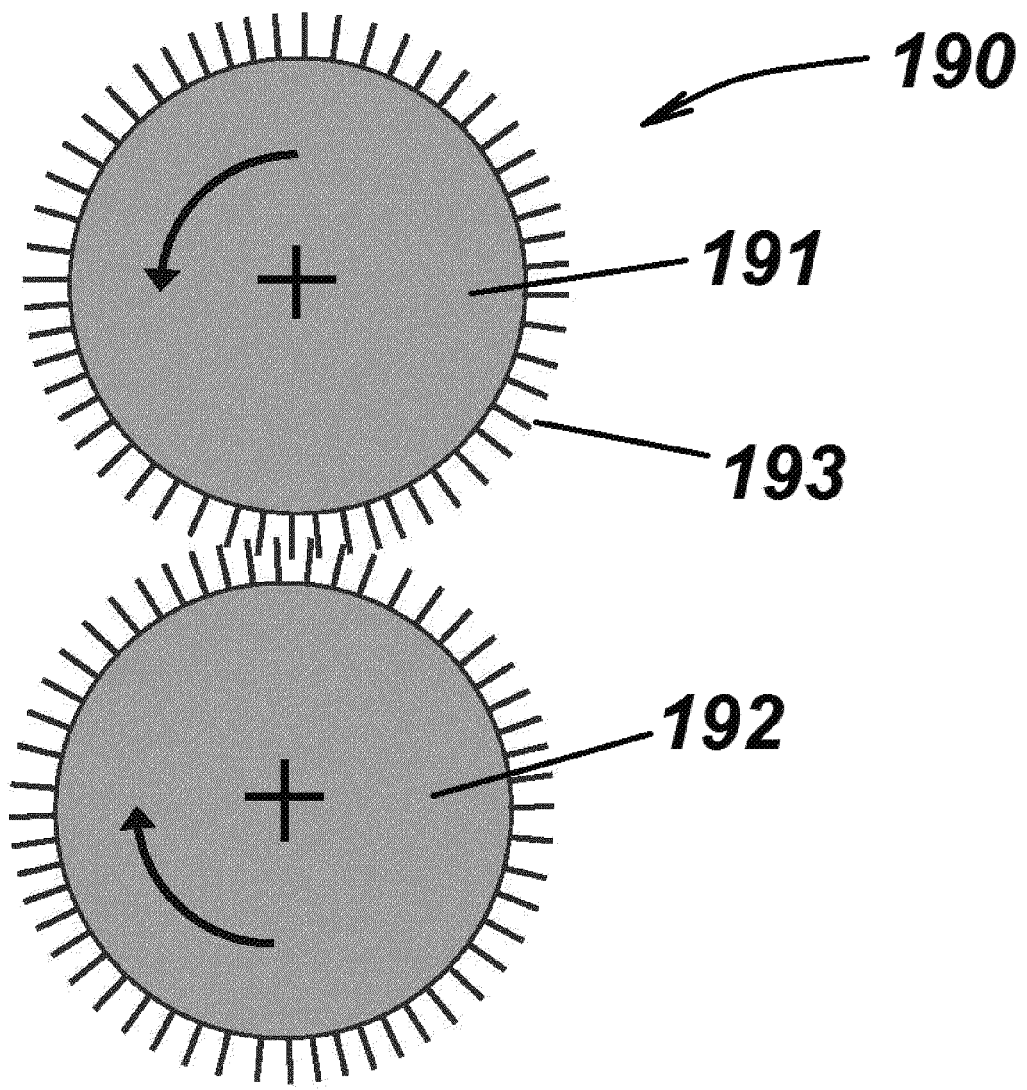
Figure 7:
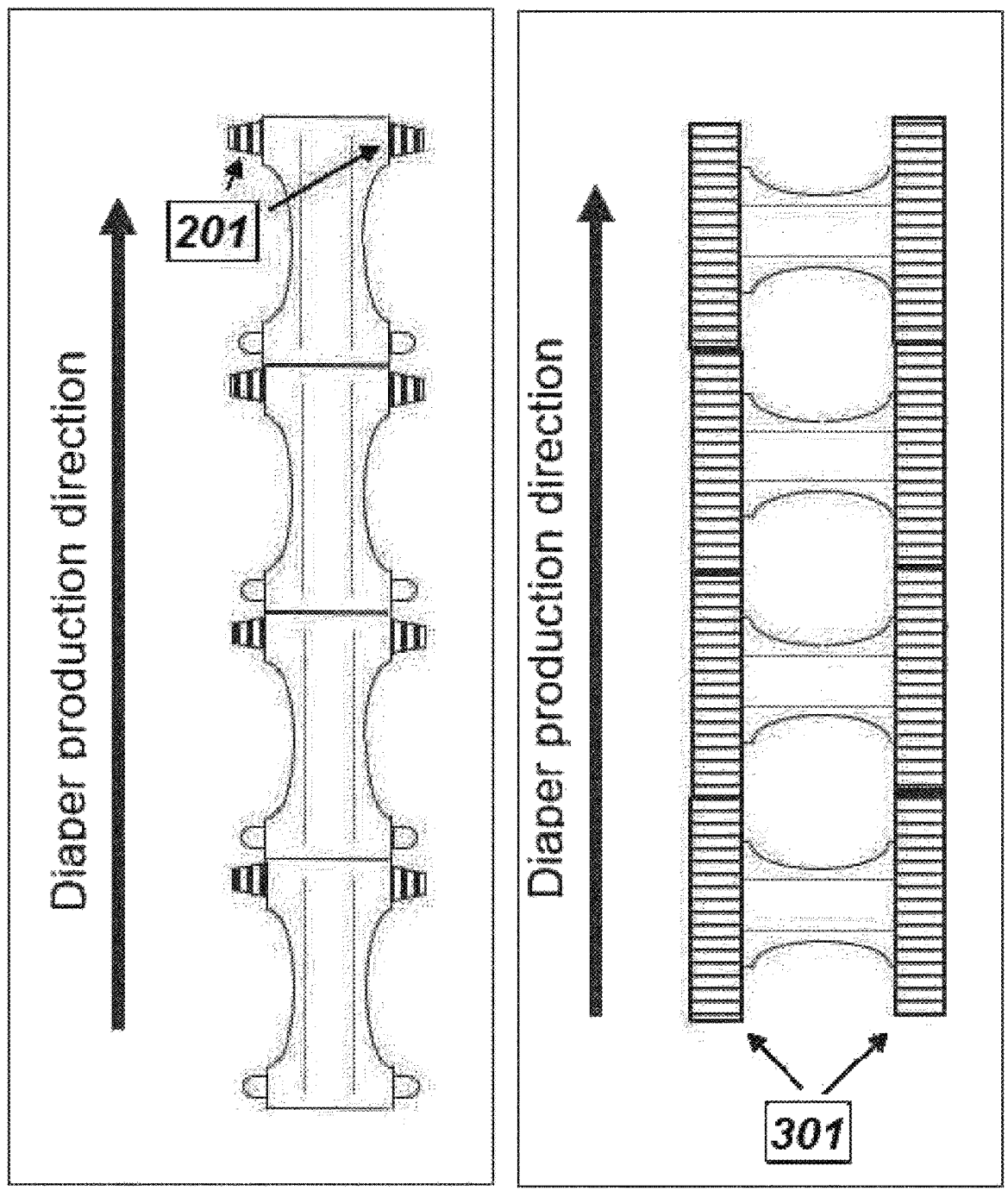
Figure 8:
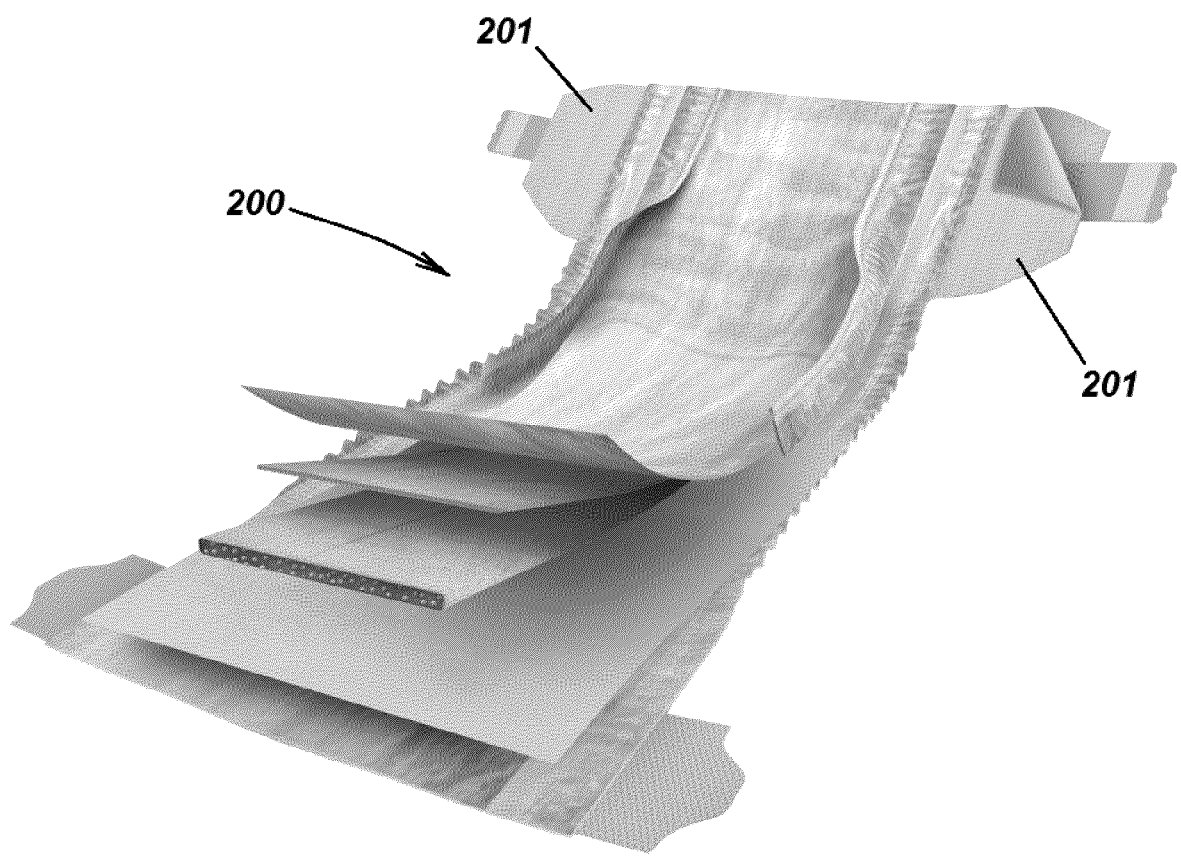
Figure 9:
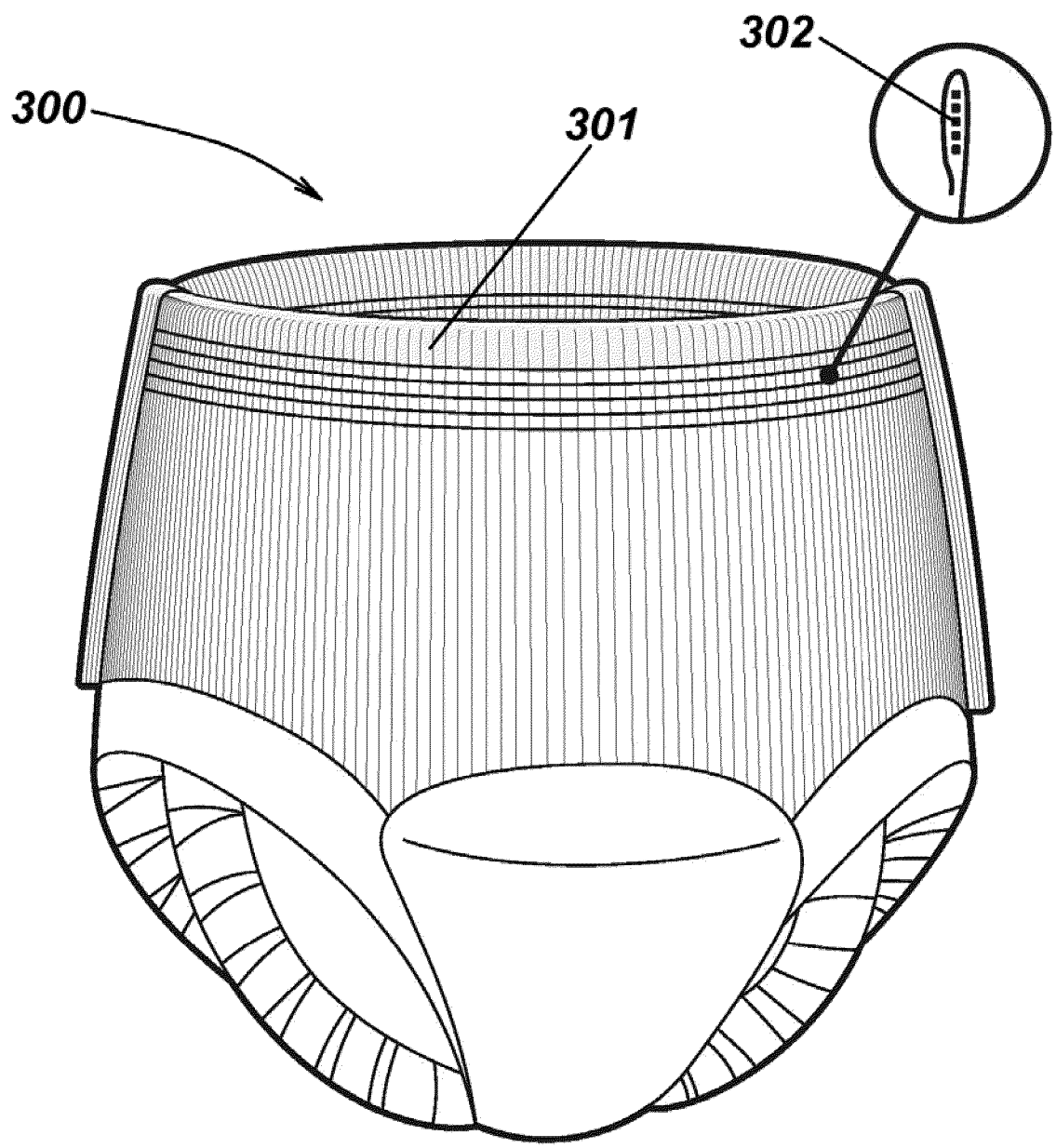
Figure 10A:
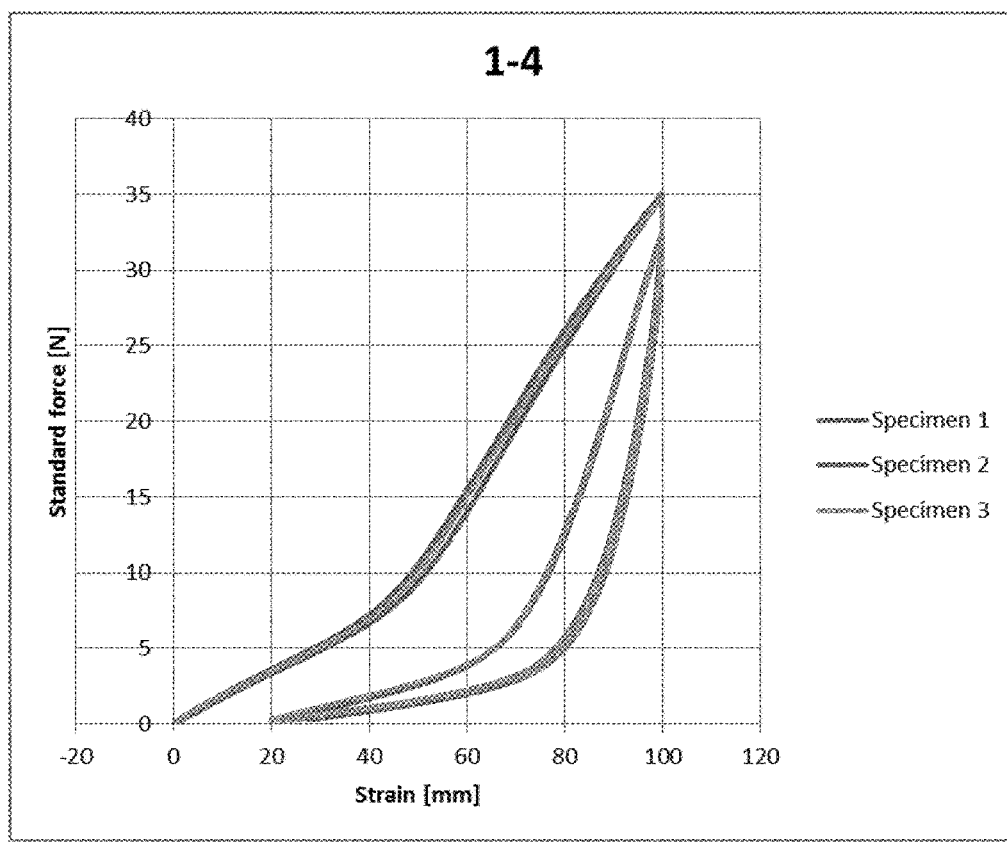
Figure 10B:
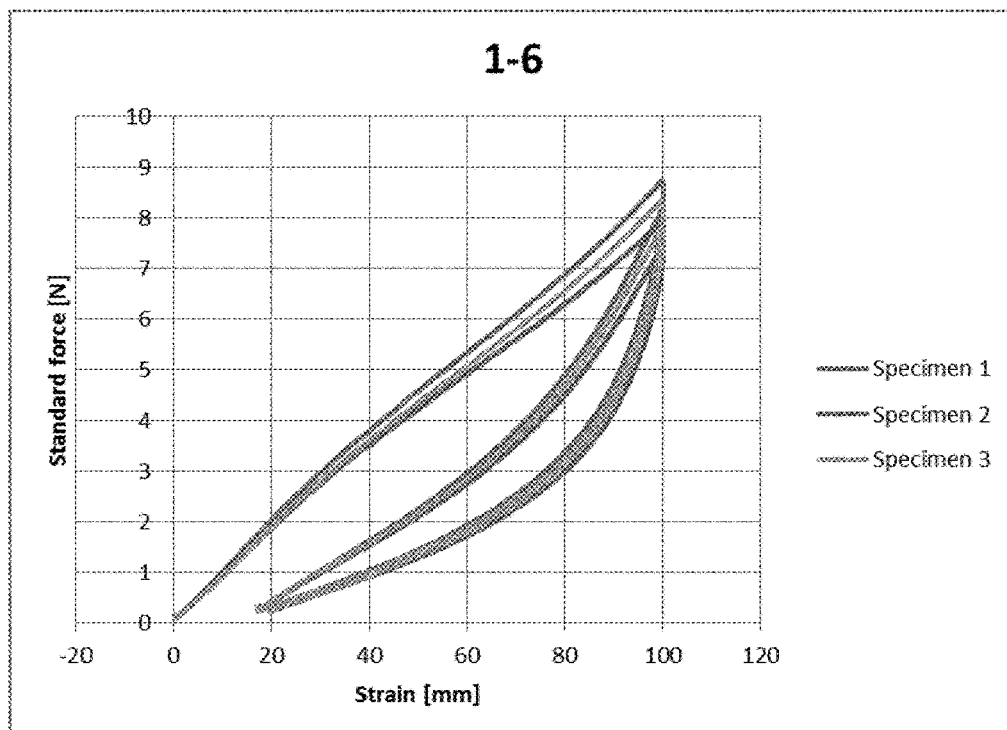
Figure 10C:
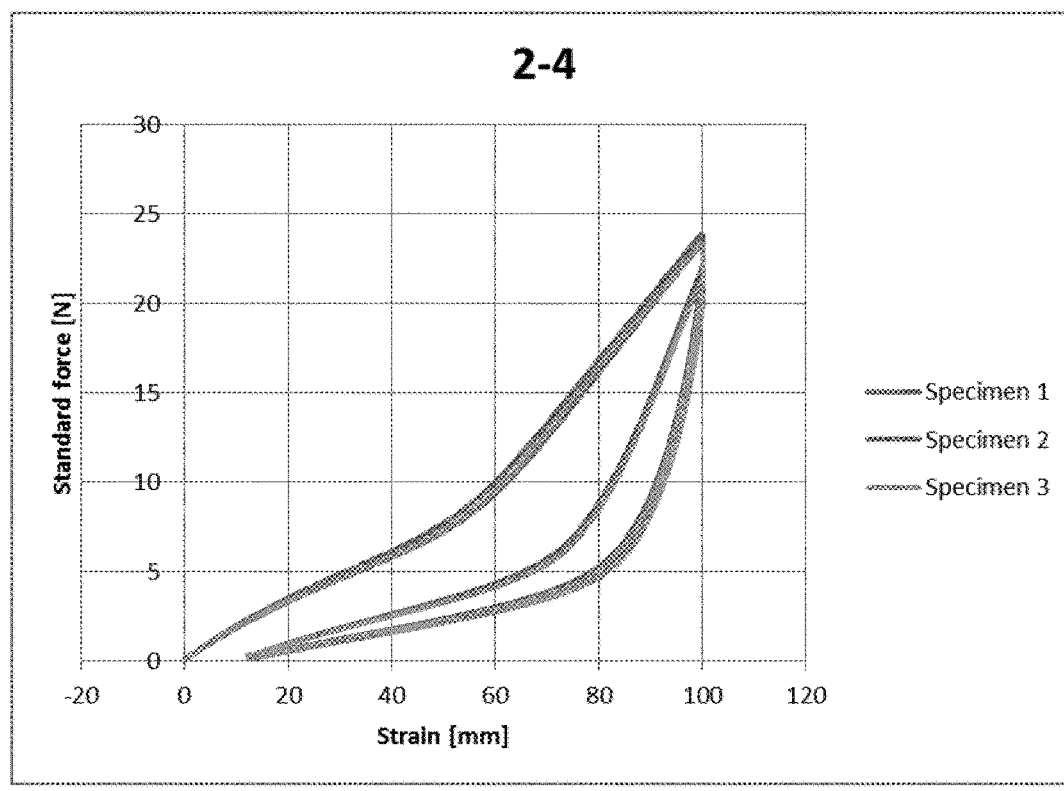
Figure 10D:
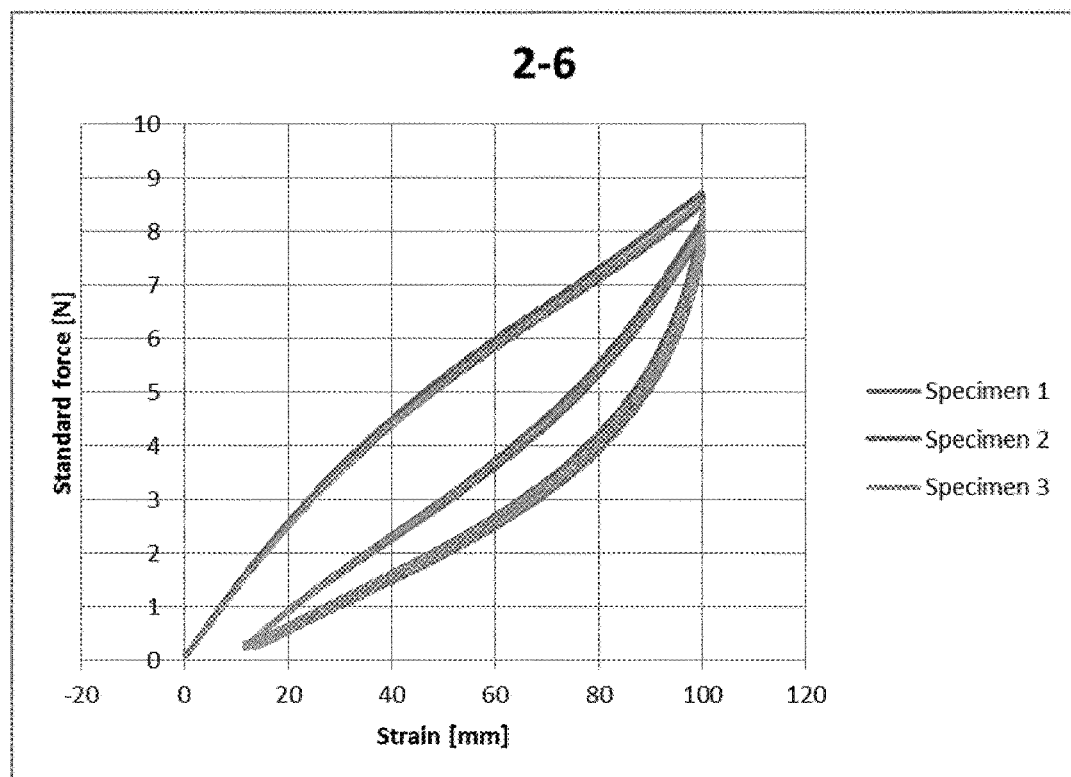
Figure 10E:
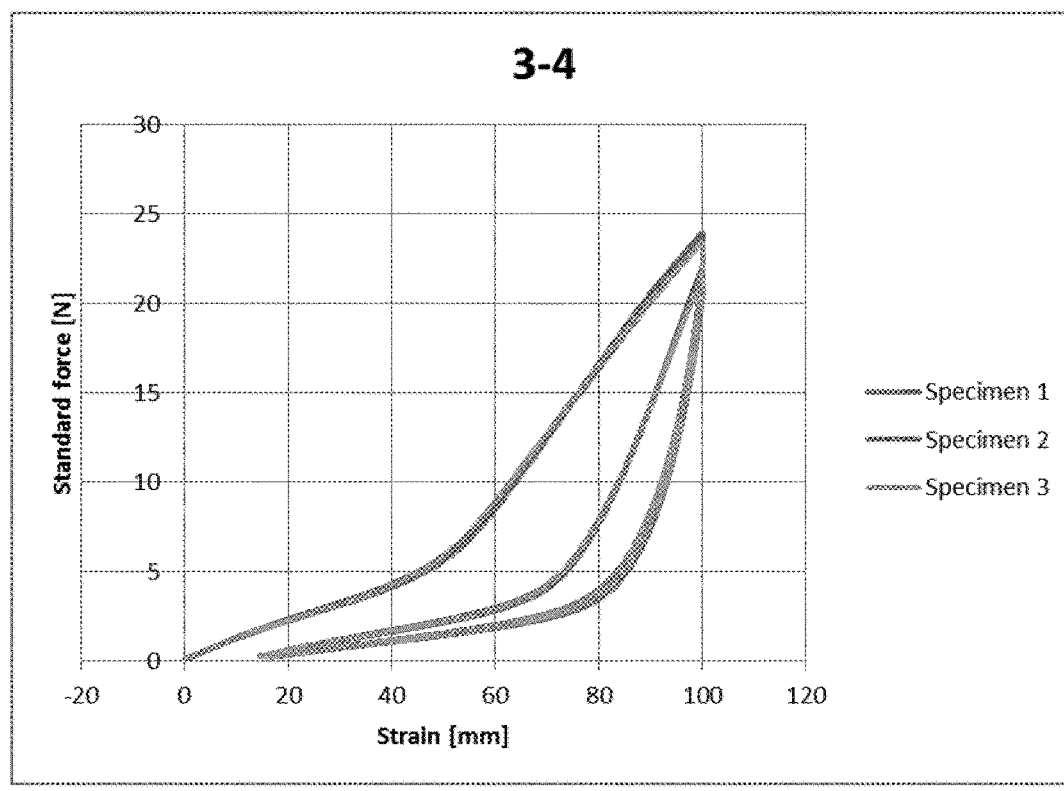
Figure 10F:
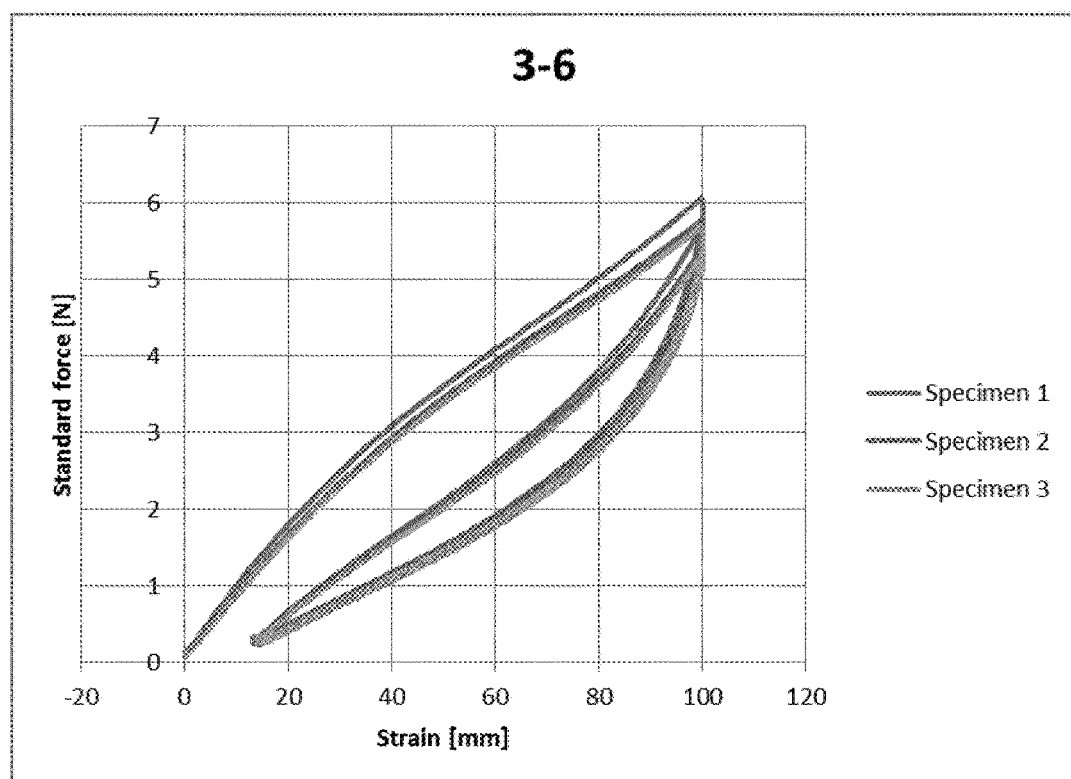
Figure 10G:
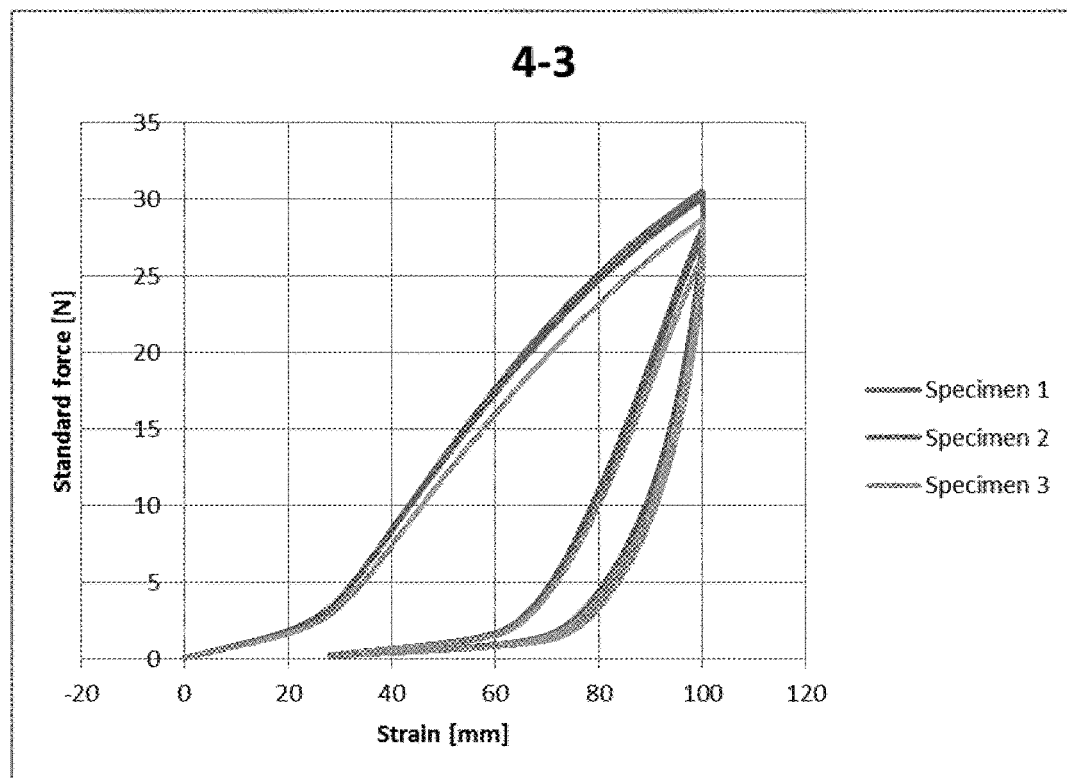
Figure 10H:
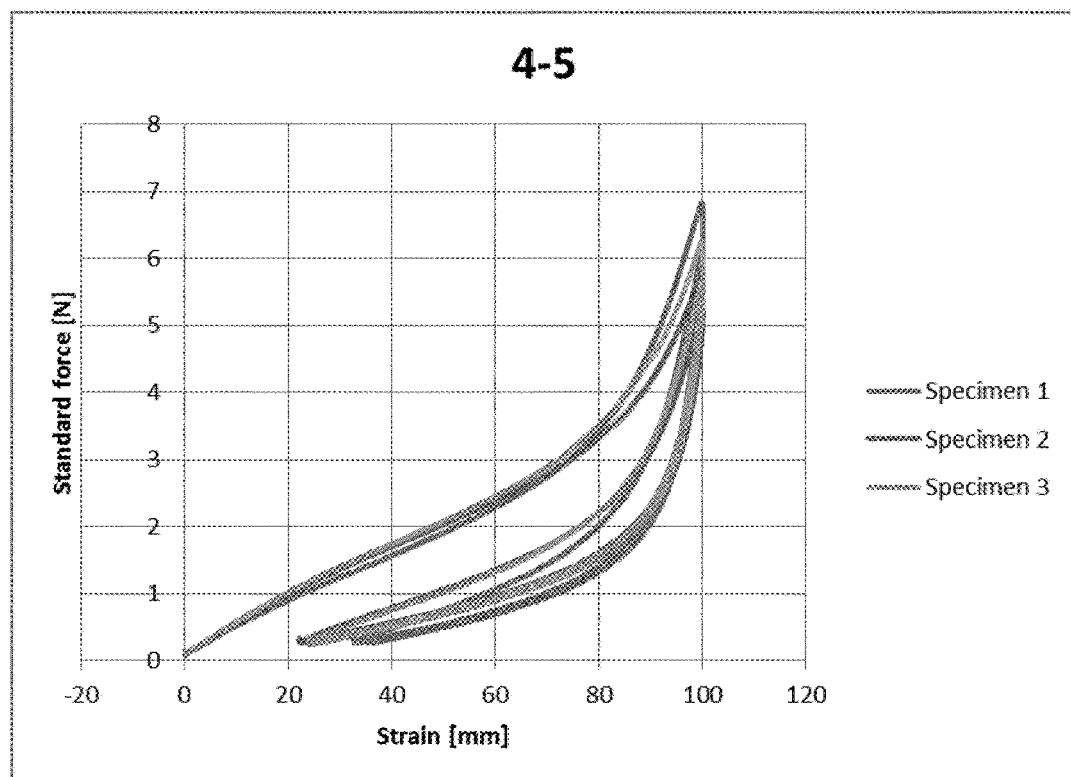
Figure 11:
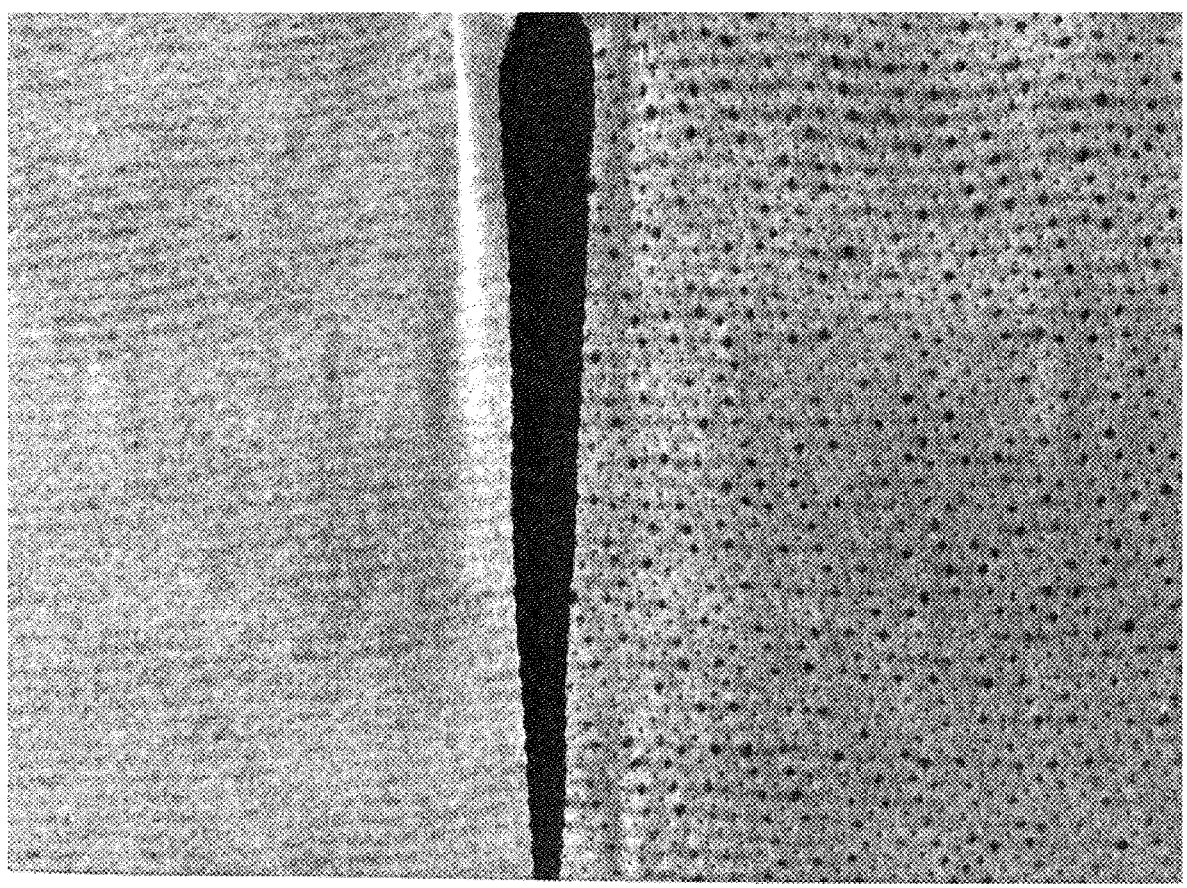
Figure 12A:
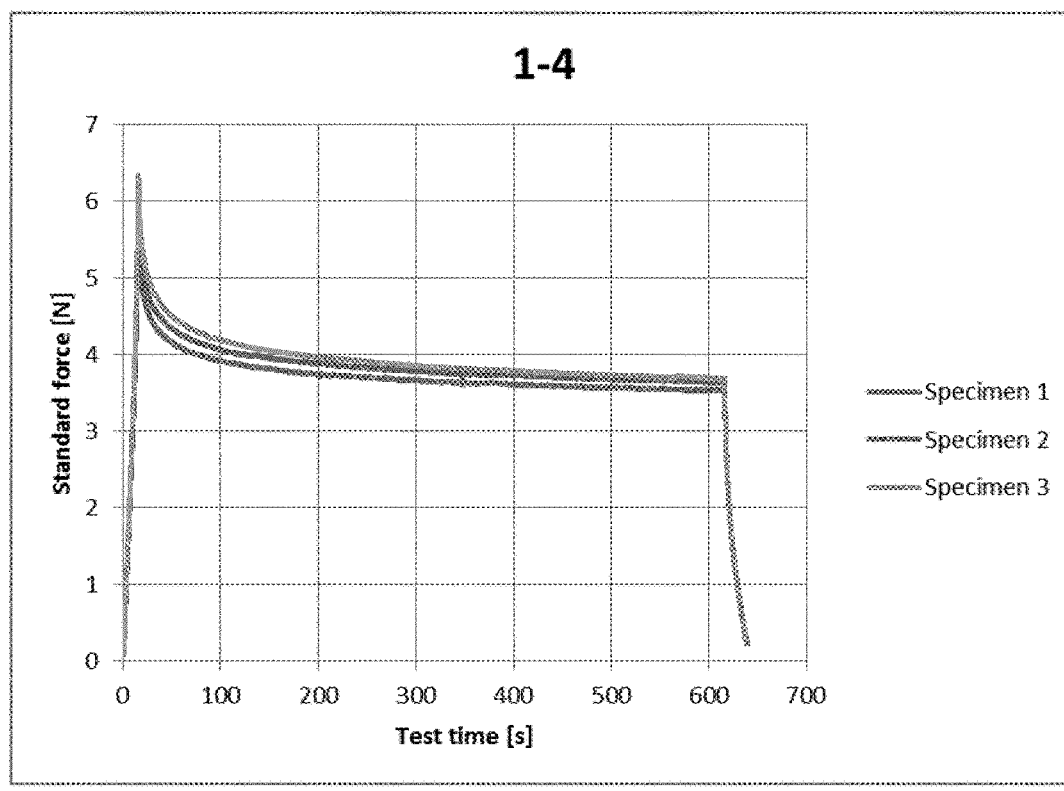
Figure 12B:
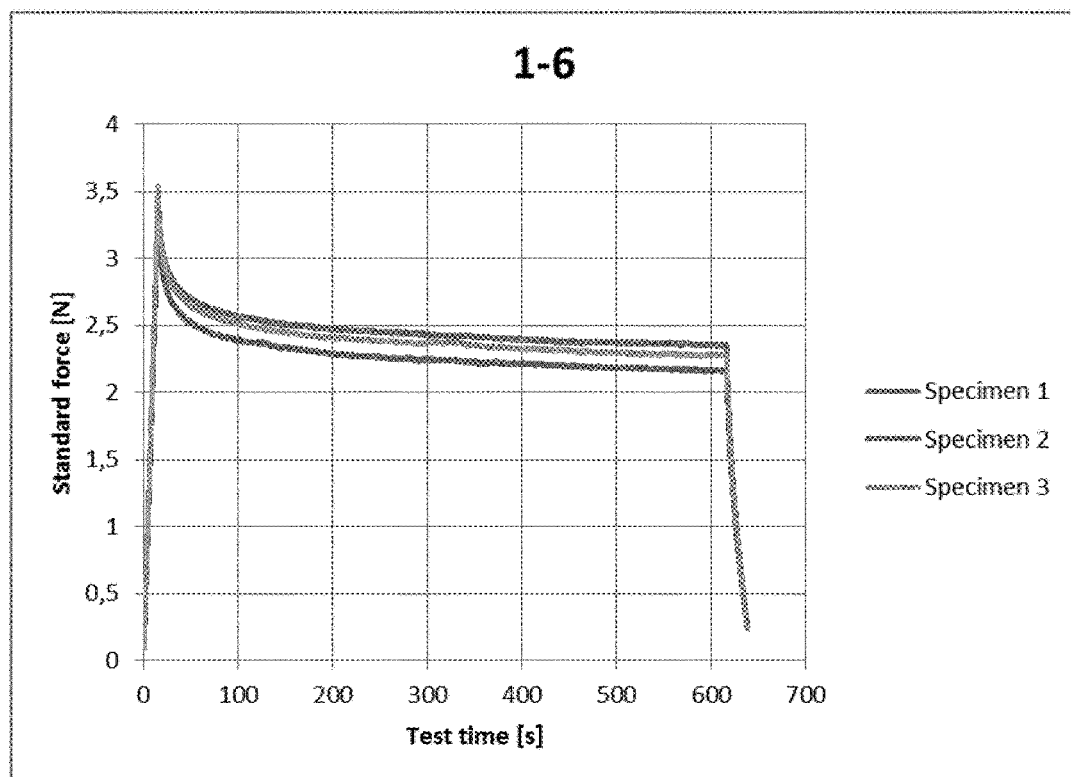
Figure 12C:
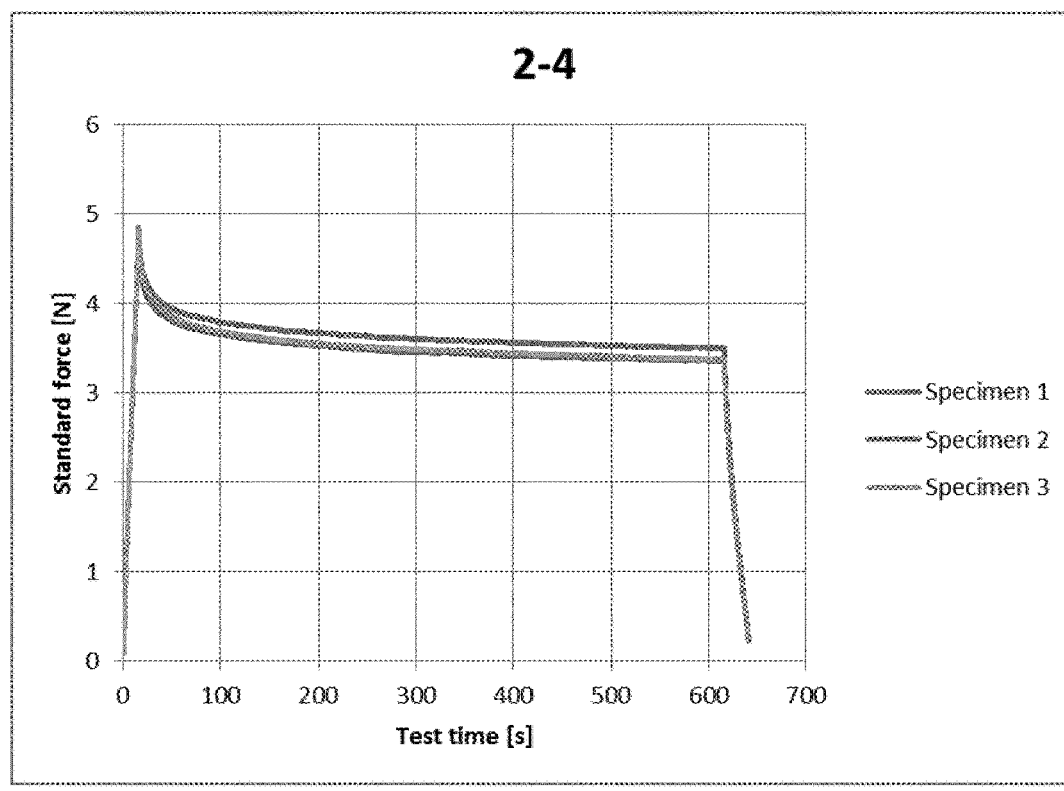
Figure 12D:
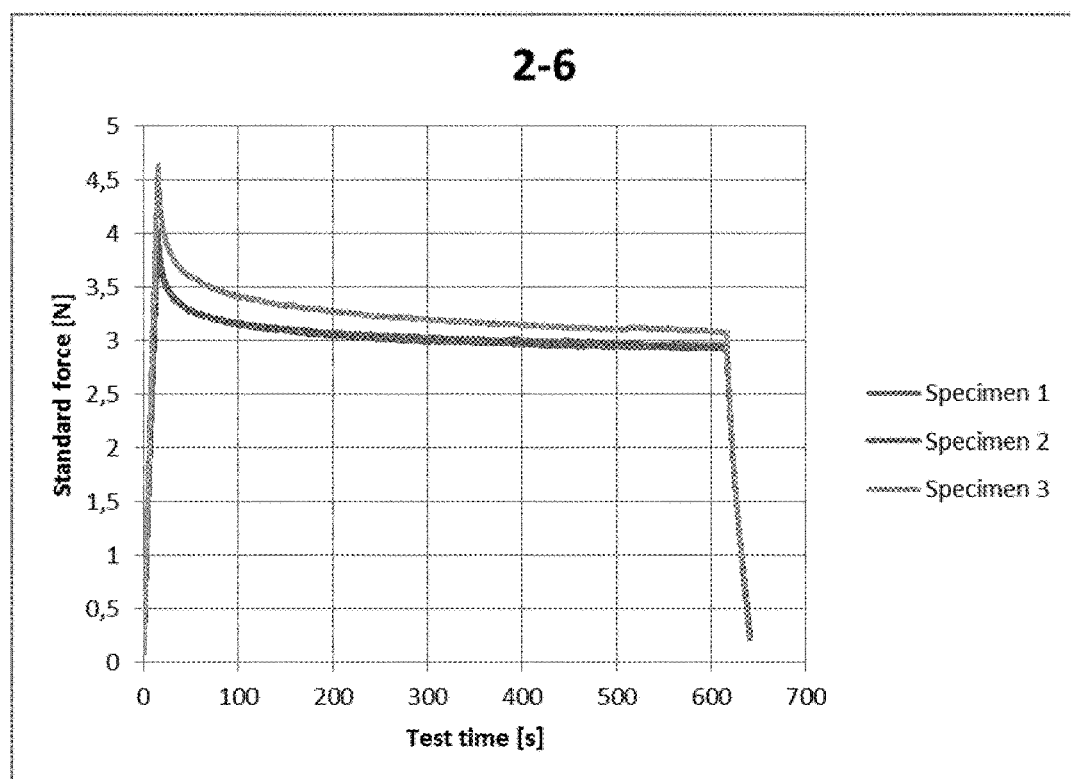
Figure 12E:
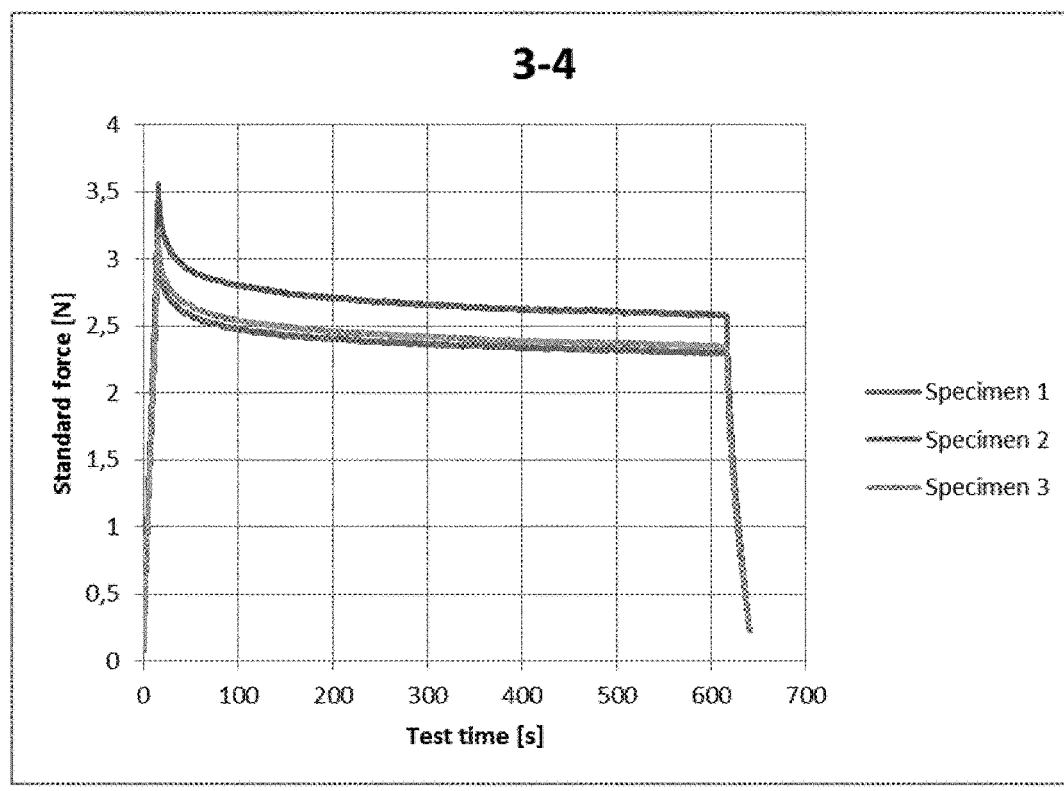
Figure 12F:
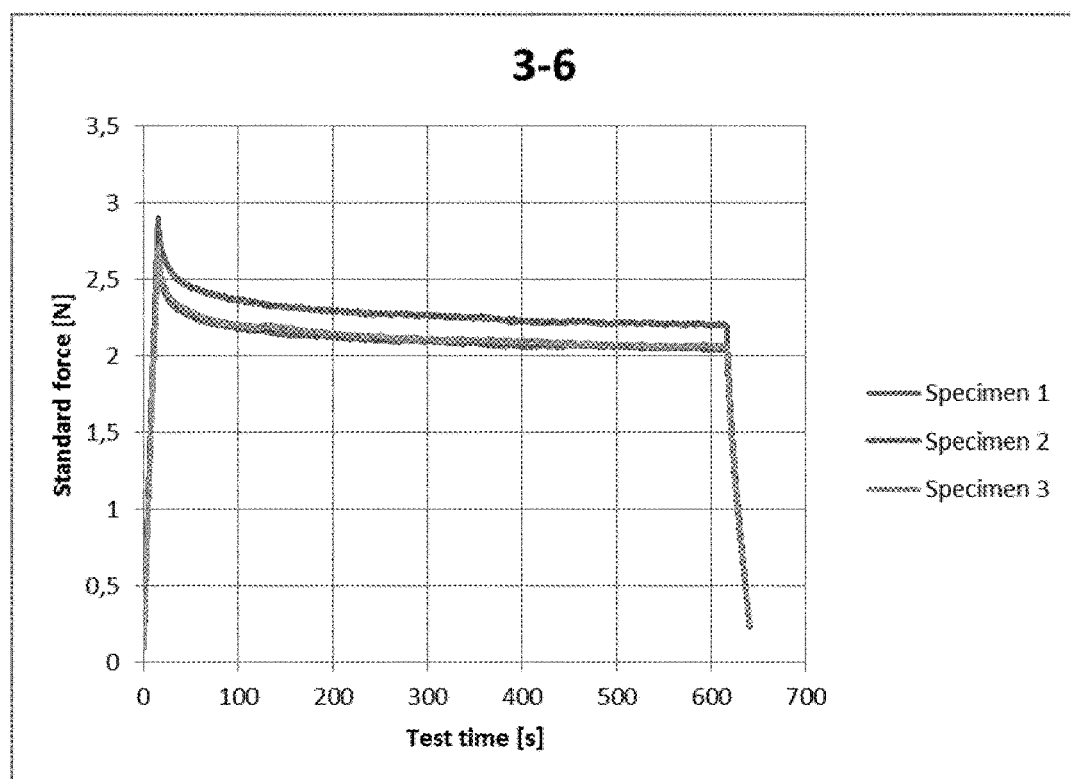
Figure 12G:
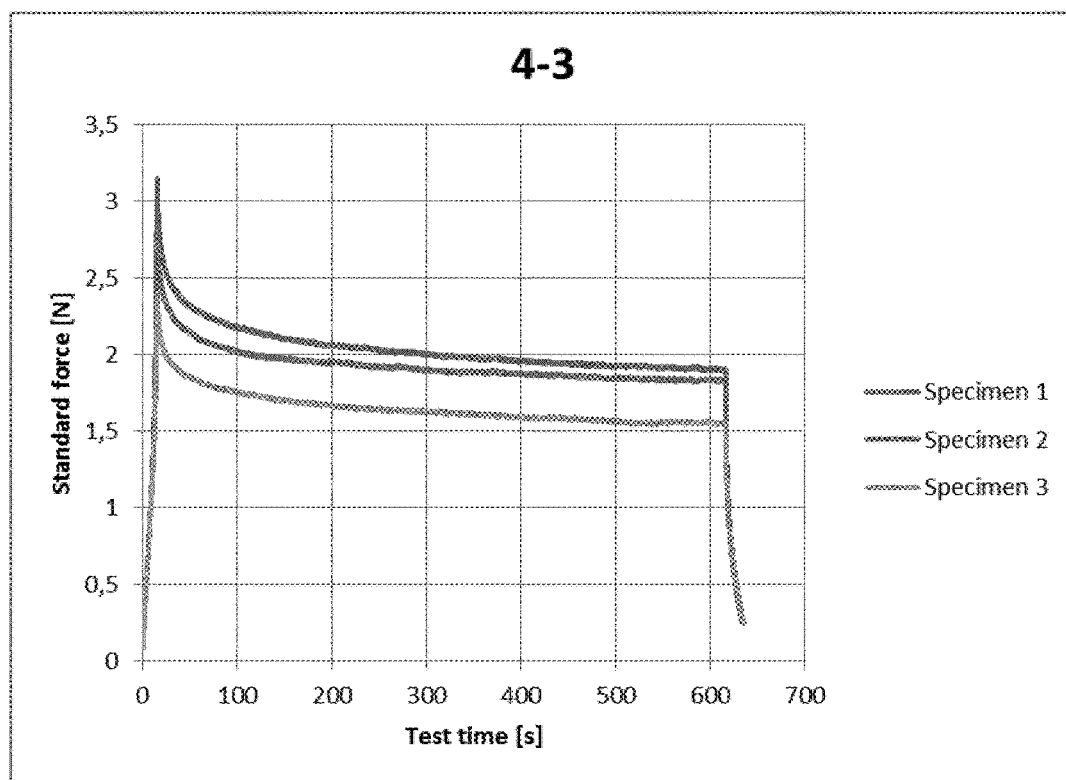
Figure 12H:
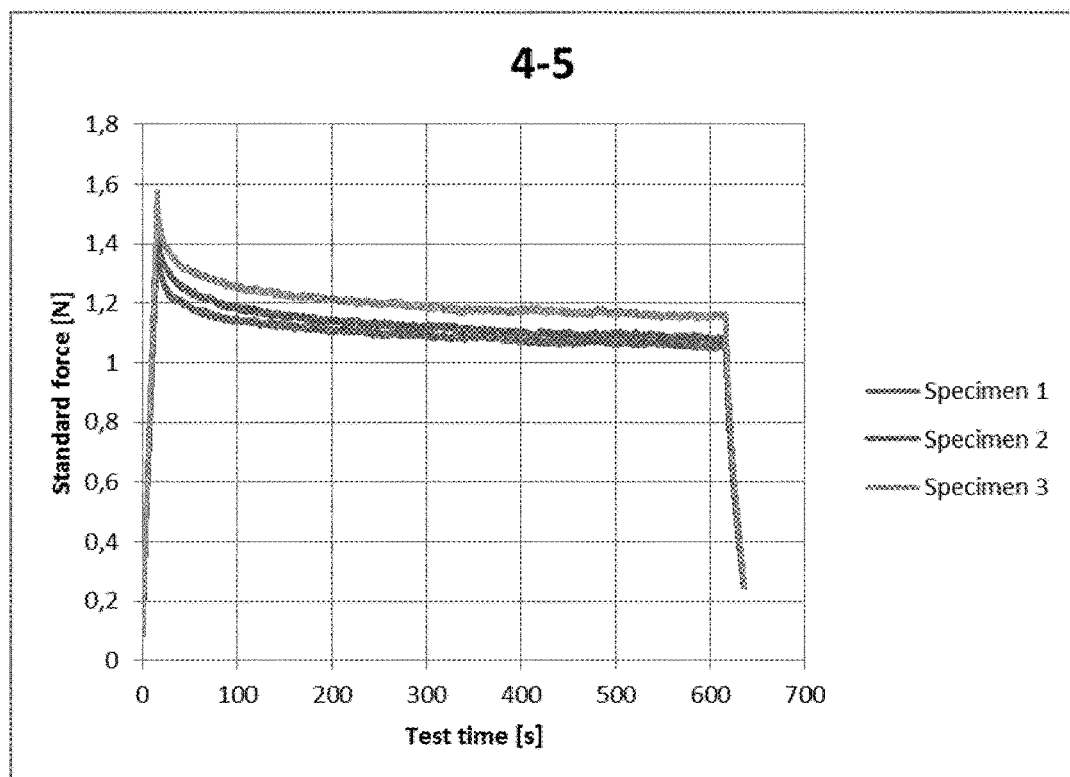

Further details and advantages of the invention will become apparent from the figures and examples described in the following. The figures show:

FIG. 1: a schematic cross-section of a nonwoven fabric of the invention;

FIG. 2: an exemplary machine setups for manufacturing nonwoven fabric sheets of the invention;

FIG. 3: another exemplary machine setups for manufacturing nonwoven fabric sheets of the invention;

FIG. 4: an illustration of a ring-rolling mill configured to activate nonwoven fabric sheets of the invention in cross-direction;

FIG. 5: an illustration of the mill of FIG. 4 in operation;

FIG. 6: an illustration of a cross-bladed mill configured to activate nonwoven fabric sheets of the invention in lengthwise direction;

FIG. 7: production examples of open/taped diapers with back ears and pant-like baby and adult incontinence diapers;

FIG. 8: an illustration of an open/taped diaper manufactured using a nonwoven material of this invention;

FIG. 9: an illustration of an adult incontinence pant manufactured using a nonwoven material of this invention;

FIGS. 10a-10h: elasticity hysteresis curves for different activated samples according to the working examples;

FIG. 11: a magnified picture of an activated sample according to one of the examples;

FIGS. 12a-12h: curves of elastic force over time for different activated samples according to the working examples.

In FIG. 1 a schematic cross-section of a sandwich-type elastic nonwoven fabric sheet is shown. The sheet, generally designated with reference numeral 100, comprises an elastic middle layer 130 that is covered with a carrier layer 110 and 120, respectively, on either side. Both carrier layers 110 and 120 are spunbonded nonwoven webs formed from crimped multicomponent fibers and at least one of the carrier layers, namely the carrier layer 110 has a regular pattern of calender bonding points. The middle layer 130 is a spunbonded nonwoven web formed from elastic fibers and is devoid of any calender bonding points. The layers 110, 120 and 130 adhere to each other without the use of glue simply due to the inherent adhesive properties of the elastic fibers of the middle layer 130.

An exemplary machine setup for manufacturing a nonwoven fabric sheet 100 as illustrated in FIG. 1 is shown in FIG. 2.

The setup comprises a conveyor belt 10 that runs from a first feed roll 20 of prefabricated carrier web to a product roll 80. Along the way, the conveyor belt passes a spinning machine 30, a second feed roll 40 of prefabricated carrier web and a pair of precompaction rollers 70. The spinning machine comprises a reservoir 31 for polymer raw materials that form for a thermoplastic elastomer component, a mixing and feeding channel 32, an extrusion die 33, a channel 34 for quenching and stretching and an air suctioning device 35 below the conveyor belt 10.

In operation, a prefabricated nonwoven web 110 is continuously unrolled from the first feed roll 20 and transported towards the spinning machine 30 on the conveyor belt 10. An elastic layer 130 is then formed by depositing elastic polymer fibers on top of the web 110 in the spinning machine 30. Another prefabricated nonwoven web 120 is concurrently unrolled from the second feed roll 40 and laid on top of the freshly formed elastic layer 130. The three-layered fabric is then slightly compressed between the pair of pre-compaction rollers 70 and the resulting sheet 100 collected on the product roll 80.

Another machine setup for manufacturing a nonwoven fabric sheet 100 as illustrated in FIG. 1 is shown in FIG. 3.

In this setup, the second feed roll is replaced by a further spinning machine 60 for in situ formation of the top carrier layer 120. The further spinning machine 60 comprises reservoirs 61a and 61b for the polymer raw materials that form for the polymer components of the bicomponent fibers, corresponding mixing and feeding channels 62a and 62b, an extrusion die 63, a channel 64 for quenching and stretching and an air suctioning device 65 below the conveyor belt 10. An additional pair of intermediate pre-compaction rollers 50 is disposed between the spinning machine 30 and the further spinning machine 60.

In operation, a prefabricated nonwoven web 110 is continuously unrolled from the first feed roll 20 and transported towards the spinning machine 30 on the conveyor belt 10. An elastic layer 130 is then formed by depositing elastic polymer fibers on top of the web 110 in the spinning machine 30. The two-layered intermediate fabric is then slightly compressed between the pair of intermediate pre-compaction rollers 50. A top carrier layer 120 is then formed by depositing crimped bicomponent fibers on top of the elastic layer 130 in the further spinning machine 60. The three-layered fabric is then slightly compressed between the pair of pre-compaction rollers 70 and the resulting sheet 100 collected on the product roll 80.

FIG. 4 shows a ring-rolling mill 90 that may be used to activate a nonwoven fabric sheet 100 of the invention, be it inline between the pre-compaction rollers 70 and the product roll 80 of the settings shown in FIGS. 2 and 3 or in a remote standalone setting. The mill 90 comprises a pair of counter-rotating rollers 91 and 92. Annular discs 93 are mounted to the surfaces of both rollers 91 and 92 to obtain a surface structure of annular grooves, i.e. the spaces between the discs, and crests, i.e. the discs 93. The discs 93 are mounted with an offset on rollers 91 and 92 and the discs 93 of one roller 91 or 92 interlock with the discs 93 of the other roller 92 or 91. In FIG. 4, the width of the discs 93 is labelled with letter "a", the depth of engagement ("DOE") is labelled with letter "b" and the disk spacing is labelled with letter "c".

FIG. 5 shows the mill of FIG. 4 in operation. A laminated sheet 100 of this invention, which is configured as shown in FIG. 1 and that may be manufactured on a line as illustrated in FIG. 2 or 3, and which comprises an elastic core formed from elastic polymer fibers and carrier layers on both surfaces is mechanically activated in a continuous manner by passing it through the spacing between the rollers 91 and 92. This activation results in an overall stretch of the sheet 100 in cross-machine direction. In more detail, the fabric 100 is stretched mainly in stress zones 101 and hardly stretched in stress-free zones 102. The stretching will alter the microscopic fiber configuration in the carrier layers 110 and 120 along stripes in machine direction, which follow the impact profile of the discs 93, while the microscopic structure of the elastic layer 130 will remain largely unaffected due to the elasticity of its fibers and due to the lack of thermal bonding.

As a measure for the level of mechanical activation, apart from the simple depth of engagement, the so-called elongation stress factor ("EFS") can be defined as follows, with the letters "a", "b" and "c" being defined as above:

$$EFS = \frac{\sqrt{(c-a)^2 + b^2} + a}{c} \times 100 = \% \quad \text{(Formula 1)}$$

FIG. 6 shows an example of a cross-bladed mill 190 configured to activate nonwoven fabric sheets 100 of the invention in lengthwise direction. Likewise mill 90, it may be positioned inline between the pre-compaction rollers 70 and the product roll 80 of the settings shown in FIGS. 2 and 3 or in a remote standalone setting. The mill 190 comprises a pair of counter-rotating rollers 191 and 192, both comprising interlocking cross-directional blades 193. This mill 190 has the ability to activate the sheet 100 by introducing alternating macroscopic zones of different microscopic fiber configuration that are in the form of parallel stripes oriented in cross-machine direction of the sheet.

The ability of the inventive material to be stretched/activated in both cross and machine direction is unique. In allows the material to be used in both open/taped diapers as back ears where cross directional extensibility is required, and as elastic waist panels in pant-like baby and adult incontinence diapers, where lengthwise stretch of materials is required, as these products are typically produced in cross direction to the machines direction on the diaper lines.

This is best seen in FIG. 7, where the left picture shows production of a traditional open/taped diaper construction is displayed, with back ears 201 where the material has been activated in cross machine direction. The right picture shows production of pant-like baby and adult incontinence diapers, where the elasticated waist panel 301 has been activated in machine direction.

FIGS. 8 and 9 illustrate products, which may be manufactured using the elastic nonwoven materials of the invention. FIG. 8 shows an open/taped baby diaper 200 with back ears 201. FIG. 9 shows a pant-like adult incontinence diaper 300 an elasticated waist panel 301 having additional elastic strands 302 for reinforcement.

EXAMPLES

An elastic nonwoven fabric sheet was prepared on a machine setup as shown in FIG. 2.

As a first prefabricated spunbonded carrier layer 110 a spunbonded sheet of crimped bicomponent fibers in a 50/50 side-by-side configuration by weight was provided. Likewise, also as a second prefabricated spunbonded carrier layer 120 a spunbonded sheet of crimped bicomponent fibers in a 50/50 by weight side-by-side configuration of polymer components A and B was provided. The polymer materials were as indicated in Table 1 below. In this context, Sabic PP511A is a commercially available polypropylene material having a relatively narrow polydispersity of between 3-5 and a melt flow rate of approx. 25 g/10 min. Sabic QR674K is a commercially available polypropylene-ethylene copolymer with a relatively broad molecular weight distribution. Lyondellbasell Moplen RP3386 is a commercially available polypropylene-ethylene copolymer with a narrower molecular weight distribution. The fifty-fifty mixture of QR674K and RP3386 leads to a polypropylene-ethylene copolymer component having a polydispersity of a bit more than 5 and a melt flow rate of approx. 30 g/10 min. The sheets 110 and 120 both had an open calendered bond pattern with a bonding area of 12% on account of 24 regularly distributed circular bonding dots per cm².

The elastic layer was made from a single commercially available TPE-o material Vistamaxx™ 7050FL from ExxonMobil, which is a propylene-based thermoplastic elastomer copolymer with an ethylene content of approx. 13 wt.-% and a melt flow rate of approx. 48 g/10 min and a softening temperature of approx. 51° C.

Unless indicated otherwise, molecular weight distributions and softening points are according to manufacturer's indication and melt flow rates are as as measured according to ISO 1133 with conditions being 230° C. and 2.16 kg.

TABLE 1

| Example # | Layer 110 g/m² | Layer 110 Polymers | Layer 120 g/m² | Layer 120 Polymers | Layer 130 g/m² | Layer 130 Polymers | Overall g/m² |
|---|---|---|---|---|---|---|---|
| 1 | 15 | A: PP511A B: 50% QR674K 50% RP3386 | 15 | A: PP511A B: 50% QR674K 50% RP3386 | 90 | 7050FL | 120 |
| 2 | 15 | A: PP511A B: 50% QR674K 50% RP3386 | 15 | A: PP511A B: 50% QR674K 50% RP3386 | 90 | 7050FL | 120 |
| 3 | 15 | A: PP511A B: 50% QR674K 50% RP3386 | 15 | A: PP511A B: 50% QR674K 50% RP3386 | 60 | 7050FL | 90 |
| 4 | 15 | A: PP511A B: 50% QR674K 50% RP3386 | 15 | A: PP511A B: 50% QR674K 50% RP3386 | 30 | 7050FL | 60 |

The extrusion temperature at the spinning machine 30 was between 235° C. and 245° C., the die had 6000 holes per linear meter and a hole diameter of 0.6 mm. The precompaction rollers 70 were set to a temperature of 60° C. and the linear pressure was set to 4 N/mm. The nonwovens of examples 2-4 were produced with pre-compaction, but without any additional calendering. The nonwoven of example 1 was subjected to additional calendering with a calender pattern of 12% open dot and 24 dots/cm².

The fiber diameters obtained in the facing layers 110 and 120 have been determined to be 1.71 denier on average. The fiber diameters obtained in the core layer 130 have been determined to be 3.71 denier on average.

Prior activation, the resulting fabrics were tested for a variety of physical parameters. The results are shown in Table 2 below.

TABLE 2

| Example # | TSMD N/50 mm | TEMD % | TSCD N/50 mm | TECD % |
|---|---|---|---|---|
| 1 | 100.5 | 59.9 | 101 | 172 |
| 2 | 75.7 | 103.2 | 49 | 182 |
| 3 | 67.3 | 102.9 | 43 | 146 |
| 4 | 62.0 | 91.8 | 38 | 134 |

| Example # | MD bending length mm | CD bending length mm | Basis weight g/m² |
|---|---|---|---|
| 1 | 84.0 | 48.2 | 119.9 |
| 2 | 83.0 | 42.7 | 119.1 |
| 3 | 71.6 | 40.0 | 90.0 |
| 4 | 68.0 | 38.1 | 60.0 |

Tensile Strength (TS) and tensile elongation (TE) in machine direction (MD) and cross-machine direction (CD) were measured in agreement with the provisions set out in WSP 100.4 at a preload tension of 0.1 N.

Bending length was measured in agreement with WSP 90.5.

The samples were subsequently activated by mechanical milling (ring-rolling) in a mill as schematically shown in FIGS. 4-5.

The configuration of the mill 90 for mechanical activation was a=0.8 mm, d (=DOE)=variable (3-6 mm) and c=3.3 mm, resulting in a maximum EFS according to Formula 1 above of 221% at DOE=6. The fabrics 1-3 withstood mechanical activation with DOE=6 mm without any shredding. The fabric 4 withstood mechanical activation with DOE=5 mm without any shredding.

The resulting activated fabrics were again tested for a variety of physical parameters. The results are shown in Table 3 below.

TABLE 3

| Example #-DOE [mm] | TSMD N/50mm | TEMD % | TSCD N/50 mm | TECD |
|---|---|---|---|---|
| 1-4 | 79.2 | 102.3 | 51.1 | 158.6 |
| 1-6 | 53.7 | 102.6 | 29.3 | 179.0 |
| 2-4 | 64.0 | 123.8 | 42.1 | 191.2 |
| 2-6 | 41.7 | 105.0 | 32.1 | 230.0 |
| 3-4 | 53.6 | 99.9 | 36.4 | 162.6 |
| 3-6 | 34.2 | 93.5 | 22.0 | 209.2 |
| 4-3 | 57.1 | 94.8 | 33.3 | 126.2 |
| 4-5 | 41.2 | 93.0 | 25.5 | 169.4 |

| Example #-DOE [mm] | MD bending length mm | CD bending length mm | Basis weight g/m² | Caliper mm | Air permeability I/(M² × min) |
|---|---|---|---|---|---|
| 1-4 | 62.8 | 27.4 | 111 | 0.782 | 441 |
| 1-6 | 53.9 | 20.3 | 101 | 0.850 | 843 |
| 2-4 | 50.8 | 24.3 | 116 | 0.784 | 556 |
| 2-6 | 51.0 | 21.1 | 108 | 0.874 | 745 |
| 3-4 | 53.9 | 25.4 | 87.5 | 0.754 | 971 |
| 3-6 | 45.3 | 20.2 | 80.6 | 0.772 | 1282 |
| 4-3 | 59.8 | 26.0 | 59.3 | 0.610 | 1818 |
| 4-5 | 51.8 | 22.8 | 57.0 | 0.742 | 2056 |

Again, tensile Strength (TS) and tensile elongation (TE) in machine direction (MD) and cross-machine direction (CD) were measured in agreement with the provisions set out in WSP 100.4 at a preload tension of 0.1 N.

Air permeability was measured in agreement with WSP 70.1 at a delta pressure of 200 Pa and a 20 cm² test head.

Bending length, again, was measured in agreement with WSP 90.5.

In addition, the so-called Martindale test (WSP 20.5) has been performed on the activated samples. The Martindale test is a rub test that tells the materials ability to withstand mechanical abrasion. This test was performed on Examples 4-3 and 4-5. For Example 4-3 the rating was 1.6 at 16 rubs and 2.0 at 60 rubs. For Example 4-3 the rating was 1.7 at 16 rubs and 2.0 at 60 rubs. The ratings are on a scale from 1-5 with 1 being the best and 5 being the worst.

The key property of the inventive nonwoven sheets is their elastic performance. For instance, if the sheet is used as a belt construction of a baby diaper pant, the sheet is overstretched when the diaper is pulled up and fitted in right position. It should then still exhibit enough reactive force to maintain the diapers position on the baby even upon movement and loading of the diaper with urine and faeces. If the sheet is used for the manufacture of back ears in open diapers, it is likewise crucial that the elastic performance is maintained after the stretching.

The tests for evaluating the elastic performance of the activated sheets presented in the following were carried out in cross-machine direction. Due to the ring rolling activation, the material is expected to have very good elastic properties especially in this direction.

A tensile tester as described in WSP 110.4 was used to obtain hysteresis curves for the activated sheets. A 50 mm wide sample of inventive sheet was tested. The clamp speed of the tester was set to 200 mm/min in the upwards direction and 100 mm/min in the downwards direction and the preload tension was set to 0.1 N. In a first cycle, the sheet was stretched to 200% (corresponding to 100% extension) and then immediately relaxed at a speed of 100 mm/min. In a second cycle, the sheet was again stretched to 200% (corresponding to 100% extension). In each cycle, the elastic restoring force was recorded as a function of the sheet extension.

The recorded physical parameters are given in Table 4 below.

TABLE 4

| Example #- DOE [mm] | $F_{max}$ at 100% $1^{st}$ cycle N/50 mm | Elongation end of $1^{st}$ cycle mm | F end of $1^{st}$ cycle N/50 mm | $F_{max}$ at 100% $2^{nd}$ cycle N/50 mm |
| --- | --- | --- | --- | --- |
| 1-4 | 33.9 | 21.8 | 0.237 | 31.6 |
| 1-6 | 8.18 | 17.8 | 0.250 | 7.71 |
| 2-4 | 22.9 | 13.0 | 0.226 | 21.1 |
| 2-6 | 8.46 | 12.1 | 0.246 | 7.96 |
| 3-4 | 23.0 | 15.0 | 0.249 | 21.2 |
| 3-6 | 5.75 | 13.7 | 0.249 | 5.40 |
| 4-3 | 28.7 | 27.8 | 0.257 | 26.5 |
| 4-5 | 5.94 | 24.3 | 0.256 | 5.44 |

| Example #- DOE [mm] | Elongation end of $2^{nd}$ cycle mm | F end of $2^{nd}$ cycle N/50 mm | Permanent set between $1^{st}$ and $2^{nd}$ cycles % |
| --- | --- | --- | --- |
| 1-4 | 24.8 | 0.235 | 3.93 |
| 1-6 | 20.3 | 0.250 | 3.09 |
| 2-4 | 14.8 | 0.235 | 2.04 |
| 2-6 | 14.0 | 0.245 | 2.12 |
| 3-4 | 17.0 | 0.232 | 2.31 |
| 3-6 | 15.4 | 0.243 | 1.96 |
| 4-3 | 31.2 | 0.255 | 4.68 |
| 4-5 | 28.0 | 0.251 | 4.88 |

The hysteresis curves for the activated samples are depicted in FIGS. 10a-10h. The three specimens correspond to three measurements on three identical samples that have been averaged to obtain the values of Table 4.

As apparent from the data of Table 4 and the curves of FIGS. 10a-10h, the sheets of example 1 (which have been calendered) exhibit a permanent set that is relatively high as compared to the permanent set of examples 2-4. A low permanent set is ideal. The activation of calendered materials can cause holes in the materials as the bonding locally consolidates the fibers from both the face layers and the elastic core layer to an extent that hardly any elasticity is locally available.

The difference between an uncalendered end product and a calendered end product becomes apparent from the magnified pictures shown in FIG. 11. On the left hand side the uncalendered product of sample 2-6 is shown. As apparent, despite the quite harsh activation conditions, no holes in the fabric are observed. On the right hand side the calendered product of sample 1-6 is shown. As apparent, in this material the activation produced holes.

As further apparent from the data of Table 4 and the curves of FIGS. 10a-10h, a deeper activation leads to improved elastic behaviour. Specifically, the examples with deeper activation show a more homogenous and even force over the stain distance from 0-100% elongation. Also, a deeper activation reduces the maximum force at 100% strain. In other words, it is possible to control the maximum force needed at certain strain level as well as the force at certain strain levels by the settings at activation.

Another evaluation that was carried out to evaluate the performance of the activated sheets of examples 1-4 is the testing of the materials for their ability to maintain a certain elastic force at a given strain over time.

In this context, a test sample from the hysteresis test is mounted in the clamps of a tensile tester. A preload of 0.1 N is applied. The samples are pulled to 50% strain at a speed of 200 mm/min. Once this level is reached, the force is measured over a period of 10 minutes and the drop in tensile force is recorded. The lower the drop, the better it is.

The obtained measurement curves for the activated samples are depicted in FIGS. 12a-12h. Again, the three specimens correspond to three measurements on three identical samples.

Further advantages of the inventive materials will be apparent from the following.

Many persons suffering from incontinence chose not to wear incontinence protecting pants due to the fact that current available pants are too thick and therefor too visible. Table 5 summarizes caliper/thickness measurements of the elastic waist panels of commercially available adult incontinence products. All measurements were carried out according to WSP120.6.

TABLE 5

| Product Caliper | Sloggi Basic Size Midi/EU 40 [mm] | Tena Silhouette Size M [mm] | Kao Relief Size 2 [mm] | Unicharm Lifree Size 2, 150 ml [mm] |
| --- | --- | --- | --- | --- |
| Upper Waist | 1.50 | 2.78 | 4.48 | 3.47 |
| Lower Waist | 0.60 | 2.02 | 2.87 | 2.97 |

The thickness in the waist region is important for the above considerations, because it is where the diaper is most visible.

The product "Sloggi Basic" is presently the most sold female brief in Europe. It is made from a woven textile based on 95% cotton and 5% elastane. The thickness in lower waist area has been measured at 0.60 mm and the thickness in the upper waist area at 1.50 mm. The increased thickness in the upper waist area results from the layering of an additional fabric for higher elasticity performance.

The further products have thicker materials in the waist region. The elasticated waist of "Tena Silhouette" is a laminate based on two outer layers of nonwovens and one elastic film as center layer. The "Kao Relief" incontinence pant is a laminate with outer layers of nonwovens and micro elastic filaments as center layer. The "Unicharm Lifree" incontinence pant is a more traditional construction with two outer layers of nonwovens and elastic strands in the center, providing the elastic performance needed. All these products have thicknesses in the waist area of more than 2 mm in the relaxed state.

The nonwoven materials of this invention allow obtaining products with waist thicknesses that are comparable to the woven-based "Sloggi Basic" female brief. As apparent from Table 3 above, activated materials of the invention have calipers in the magnitude of 0.6-0.9 mm, depending on basis weight. When folded as visible in the exemplary incontinence pant 300 shown in FIG. 9 already discussed further above, such a material with a basis weights of approx. 90 gsm would be sufficient from a mechanical stand-point to meet the elastic requirements of adult incontinence pants, and such material has been determined to have thicknesses of around 0.75 mm. The waist belt 301 made by a double folded material layer and having a vertical dimension of around 1-4 mm will then have thicknesses in a magnitude of around 1.50 mm, just like the woven-based "Sloggi Basic" female brief, which allows much of a regular brief style look of the products. It is a major advantage for customers if the thickness of diaper products can be reduced to the thickness of regular brief products. For additional elastic force, elastic strands 302 could optionally be incorporated into the fold, as shown in the magnified portion of FIG. 9.

The invention claimed is:

1. A nonwoven fabric sheet comprising at least three adjacent layers of spunbonded nonwoven webs,
   wherein a first one of the three layers is a first carrier layer in the form of a spunbonded nonwoven web comprising crimped multicomponent fibers,
   wherein a second one of the three layers is an elastic layer in the form of a spunbonded nonwoven web comprising elastic fibers formed from a thermoplastic elastomer polymer material;
   wherein a third one of the three layers is a second carrier layer in the form of a spunbonded nonwoven web comprising crimped multicomponent fibers, and wherein the elastic layer is sandwiched between the first and second carrier layer; and
   wherein the web of each of the first carrier layer and the second carrier layer comprises a pattern of macroscopic bonding points, while the web of the elastic layer is devoid of macroscopic bonding points, and the elastic layer is adhered to each of the first carrier layer and the second carrier layer due strictly to an initial tackiness of the elastic layer.

2. The nonwoven fabric sheet of claim 1, wherein the spunbonded nonwoven web of each of the first carrier layer and the second carrier layer comprises a pattern of macroscopic bonding points.

3. The nonwoven fabric sheet of claim 1, wherein the average crimp number of the crimped multicomponent fibers is in the range of at least 5 crimps per cm in the fiber.

4. The nonwoven fabric sheet of claim 1, wherein the basis weight of each of the first carrier layer and the second carrier layer is between 5-40 g/m$^2$ and/or wherein the basis weight of the elastic layer is between 10-140 g/m$^2$.

5. The nonwoven fabric sheet of claim 1, wherein the overall thickness of the nonwoven fabric sheet is less than 1.20 mm.

6. The nonwoven fabric sheet of claim 1, wherein each of the first carrier layer and the second carrier layer comprises, a different average crimp level.

7. The nonwoven fabric sheet of claim 1, wherein at least portions of the nonwoven fabric sheet comprise alternating zones in the form of parallel stripes oriented in a lengthwise direction of the sheet, or in the form of parallel stripes oriented in a cross direction of the sheet.

8. The nonwoven fabric sheet of claim 7, wherein the fabric comprises at least one machine-directional band of activated material and at least one adjacent machine-directional band of unactivated material.

9. The nonwoven fabric sheet of claim 1, wherein the thermoplastic elastomer polymer material forming for the elastic fibers of the elastic layer is a thermoplastic polyolefin elastomer material (TPE-o).

10. The nonwoven fabric sheet of claim 1, wherein at least some of the elastic fibers of the elastic layer are bicomponent fibers comprising two distinct zones of thermoplastic elastomer of different properties.

11. The nonwoven fabric sheet of claim 1, wherein up to 20 wt.-% of a thermoplastic olefin is added to the thermoplastic elastomer of the elastic fibers of the elastic layer.

12. A method for manufacturing the nonwoven fabric sheet of claim 1, wherein the method comprises:
    (a) providing the first spunbonded nonwoven web comprising crimped multicomponent fibers, which corresponds to the first carrier layer of the nonwoven fabric sheet to be formed;
    (b) spinning and laying elastic fibers onto the first spunbonded nonwoven web to form the elastic layer of the nonwoven fabric sheet to be formed; and
    (c) superimposing a second spunbonded nonwoven web comprising crimped multicomponent fibers to the exposed side of the elastic layer to form the second carrier layer of the nonwoven fabric sheet, wherein
    the nonwoven fabric sheet is not subjected to any bonding steps after step (c).

13. The method of claim 12, wherein the first spunbonded nonwoven web is provided by unrolling from a roll of a prefabricated material.

14. The method of claim 12, wherein the second spunbonded nonwoven web is provided by unrolling from a roll of a prefabricated material.

15. The method of claim 12, wherein the second spunbonded nonwoven web is provided by spinning and laying the fibers forming for the second spunbonded nonwoven web directly to the exposed side of the elastic layer.

16. The method of claim 12, wherein the any bonding steps are patterned calendering, an application of glue, or both and the method further comprises:
    (d) pre-compacting with un-patterned rollers the nonwoven fabric sheet.

17. The method of claim 12, wherein the method further comprises:
    (e) mechanically activating the nonwoven fabric sheet in a mill comprising a pair of interacting rolls whose surfaces comprise interlocking annular grooves and crests.

18. The method of claim 12, wherein the method further comprises:
(e') mechanically activating the nonwoven fabric sheet in a mill comprising a pair of interacting rolls whose surfaces comprise interlocking cross-directional blades.

19. A hygiene article comprising the nonwoven fabric sheet according to claim 1.

20. A taped diaper comprising the nonwoven fabric sheet according to claim 1 as an elastic back ear material.

21. A diaper pant comprising the nonwoven fabric sheet according to claim 1 as an elastic waist material.

* * * * *